(12) United States Patent
Raman

(10) Patent No.: US 12,190,879 B2
(45) Date of Patent: Jan. 7, 2025

(54) CONTROLLING DEVICE OUTPUT ACCORDING TO A DETERMINED CONDITION OF A USER

(71) Applicant: GOOGLE LLC, Mountain View, CA (US)

(72) Inventor: Tiruvilwamalai Raman, San Jose, CA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 17/891,319

(22) Filed: Aug. 19, 2022

(65) Prior Publication Data

US 2022/0406307 A1 Dec. 22, 2022

Related U.S. Application Data

(63) Continuation of application No. 16/819,316, filed on Mar. 16, 2020, now Pat. No. 11,423,899, which is a continuation of application No. 16/251,943, filed on Jan. 18, 2019, now Pat. No. 10,657,968.

(60) Provisional application No. 62/769,200, filed on Nov. 19, 2018.

(51) Int. Cl.
| | |
|---|---|
| *G08B 23/00* | (2006.01) |
| *A61B 5/00* | (2006.01) |
| *A61M 21/02* | (2006.01) |
| *G10L 15/22* | (2006.01) |
| *H04N 21/485* | (2011.01) |

(Continued)

(52) U.S. Cl.
CPC ............ *G10L 15/22* (2013.01); *A61B 5/0024* (2013.01); *A61M 21/02* (2013.01); *H04N 21/4852* (2013.01); *H04N 21/4854* (2013.01); *H04N 21/8456* (2013.01); *A61M 2021/0027* (2013.01)

(58) Field of Classification Search
CPC ...... G10L 15/22; A61B 5/0024; A61M 21/02; A61M 2021/0027; H04N 21/4852; H04N 21/4854; H04N 21/8456
See application file for complete search history.

(56) References Cited

U.S. PATENT DOCUMENTS

| | | | | |
|---|---|---|---|---|
| 4,228,806 A | * | 10/1980 | Lidow | A61B 5/372 368/244 |
| 5,008,865 A | * | 4/1991 | Shaffer | G04G 11/00 368/10 |

(Continued)

FOREIGN PATENT DOCUMENTS

| | | |
|---|---|---|
| CN | 102065350 | 5/2011 |
| CN | 108234738 | 6/2018 |

OTHER PUBLICATIONS

IP.com; Method and Apparatus for Dynamic Media Control; dated 2010.

(Continued)

*Primary Examiner* — Quang Pham
(74) *Attorney, Agent, or Firm* — Gray Ice Higdon

(57) ABSTRACT

Dynamically controlling output from a device, such as an automated assistant device. Control of the output can be based on, for example, a condition and/or physiological attribute(s) of a user of the device. Various implementations dynamically control the output to improve sleep quality for the user and/or mitigate waste of computational and/or network resources.

20 Claims, 7 Drawing Sheets

(51) Int. Cl.
*H04N 21/845* (2011.01)
*A61M 21/00* (2006.01)

(56) References Cited

U.S. PATENT DOCUMENTS

| | | | | |
|---|---|---|---|---|
| 5,999,611 | A * | 12/1999 | Tatchell | H04M 3/42204 |
| | | | | 379/88.01 |
| 6,218,947 | B1 * | 4/2001 | Sutherland | G08B 21/06 |
| | | | | 340/545.4 |
| 6,697,614 | B2 | 2/2004 | Dorenbosch | H04M 3/566 |
| | | | | 455/518 |
| 8,595,771 | B1 * | 11/2013 | Sharma | H04N 21/435 |
| | | | | 725/38 |
| 9,087,515 | B2 * | 7/2015 | Tsuda | G10L 15/06 |
| 9,094,539 | B1 * | 7/2015 | Noble | H04N 21/00 |
| 9,111,542 | B1 * | 8/2015 | Hart | G10L 21/00 |
| 9,147,054 | B1 * | 9/2015 | Beal | G06F 21/32 |
| 9,171,546 | B1 * | 10/2015 | Pike | H04M 3/4936 |
| 9,325,749 | B2 * | 4/2016 | Bangor | H04L 65/403 |
| 9,368,105 | B1 * | 6/2016 | Freed | G10L 15/22 |
| 9,443,198 | B1 * | 9/2016 | Vitaladevuni | G06F 18/2148 |
| 9,471,212 | B2 * | 10/2016 | Chiu | H04M 1/724 |
| 9,665,169 | B1 * | 5/2017 | Dai | A61B 5/6898 |
| 9,697,828 | B1 * | 7/2017 | Prasad | G10L 15/08 |
| 9,779,757 | B1 * | 10/2017 | Blanksteen | G10L 15/22 |
| 9,826,372 | B2 * | 11/2017 | Jeong | G10L 15/26 |
| 9,936,068 | B2 * | 4/2018 | Kau | H04M 3/42093 |
| 10,013,999 | B1 * | 7/2018 | Fadell | H04R 1/028 |
| 10,192,546 | B1 * | 1/2019 | Piersol | G10L 15/08 |
| 10,297,250 | B1 * | 5/2019 | Blanksteen | G10L 15/32 |
| 10,593,328 | B1 * | 3/2020 | Wang | H04L 65/1059 |
| 10,622,004 | B1 * | 4/2020 | Zhang | G10L 25/78 |
| 10,657,981 | B1 * | 5/2020 | Mansour | H04R 3/005 |
| 10,789,948 | B1 * | 9/2020 | Klein | G06F 16/3329 |
| 10,811,002 | B2 * | 10/2020 | Cho | G10L 15/183 |
| 10,824,921 | B2 * | 11/2020 | Bathiche | G06V 20/40 |
| 10,831,839 | B1 * | 11/2020 | Ogawa | G10L 13/033 |
| 10,885,910 | B1 * | 1/2021 | Antos | G06F 3/167 |
| 10,887,764 | B1 * | 1/2021 | Mokady | H04W 4/14 |
| 10,950,228 | B1 * | 3/2021 | Tan | G06F 3/167 |
| 10,972,556 | B1 * | 4/2021 | Cheng | H04L 67/52 |
| 10,978,062 | B1 * | 4/2021 | Vanderschaegen | H04N 21/4131 |
| 11,055,355 | B1 * | 7/2021 | Monti | G06F 16/90332 |
| 11,100,922 | B1 * | 8/2021 | Mutagi | G06F 3/167 |
| 11,373,645 | B1 * | 6/2022 | Mathew | G10L 15/1815 |
| 11,410,638 | B1 * | 8/2022 | Bhatnagar | G10L 13/08 |
| 11,854,040 | B1 * | 12/2023 | George | G10L 15/22 |
| 2003/0026392 | A1 * | 2/2003 | Brown | H04M 3/42221 |
| | | | | 379/88.13 |
| 2003/0072429 | A1 * | 4/2003 | Slobodin | H04M 7/128 |
| | | | | 379/202.01 |
| 2003/0182123 | A1 * | 9/2003 | Mitsuyoshi | G10L 17/26 |
| | | | | 704/E13.004 |
| 2004/0052218 | A1 * | 3/2004 | Knappe | H04M 3/42187 |
| | | | | 370/266 |
| 2007/0058795 | A1 * | 3/2007 | Arrant | H04M 3/56 |
| | | | | 379/202.01 |
| 2007/0127656 | A1 * | 6/2007 | Citron | H04M 3/4211 |
| | | | | 379/142.01 |
| 2007/0172047 | A1 * | 7/2007 | Coughlan | H04M 3/56 |
| | | | | 379/202.01 |
| 2008/0015863 | A1 * | 1/2008 | Agapi | G10L 15/22 |
| | | | | 704/E15.04 |
| 2009/0022329 | A1 * | 1/2009 | Mahowald | H03G 3/32 |
| | | | | 381/57 |
| 2009/0232481 | A1 * | 9/2009 | Baalbergen | H04N 21/8455 |
| | | | | 386/328 |
| 2010/0150333 | A1 | 6/2010 | Goodman et al. | |
| 2011/0160619 | A1 * | 6/2011 | Gabara | A61B 5/4806 |
| | | | | 600/595 |
| 2012/0078997 | A1 * | 3/2012 | Evans | G06Q 10/00 |
| | | | | 709/203 |
| 2012/0092171 | A1 * | 4/2012 | Hwang | G16H 50/20 |
| | | | | 340/575 |
| 2012/0173244 | A1 * | 7/2012 | Kwak | G10L 15/22 |
| | | | | 704/E15.001 |
| 2012/0303476 | A1 * | 11/2012 | Krzyzanowski | G06F 16/00 |
| | | | | 705/26.61 |
| 2012/0331112 | A1 * | 12/2012 | Chatani | G06F 16/435 |
| | | | | 709/219 |
| 2013/0024197 | A1 * | 1/2013 | Jang | H04N 21/4828 |
| | | | | 704/E15.001 |
| 2013/0094656 | A1 * | 4/2013 | Fung | H03G 3/3005 |
| | | | | 901/47 |
| 2013/0132081 | A1 * | 5/2013 | Ryu | H04N 21/6587 |
| | | | | 704/235 |
| 2013/0145271 | A1 * | 6/2013 | Desai | H04M 1/72451 |
| | | | | 715/727 |
| 2013/0325484 | A1 * | 12/2013 | Chakladar | G10L 15/26 |
| | | | | 704/275 |
| 2014/0156279 | A1 * | 6/2014 | Okamoto | H04M 3/4938 |
| | | | | 704/257 |
| 2014/0172953 | A1 * | 6/2014 | Blanksteen | H04L 51/18 |
| | | | | 709/203 |
| 2014/0181865 | A1 * | 6/2014 | Koganei | H04N 21/4312 |
| | | | | 725/38 |
| 2014/0222436 | A1 * | 8/2014 | Binder | G10L 15/22 |
| | | | | 704/275 |
| 2014/0229184 | A1 * | 8/2014 | Shires | H04L 12/282 |
| | | | | 704/275 |
| 2014/0250477 | A1 * | 9/2014 | Kang | H04N 21/42222 |
| | | | | 725/110 |
| 2014/0273979 | A1 * | 9/2014 | Van Os | H04M 3/533 |
| | | | | 455/412.2 |
| 2014/0278438 | A1 * | 9/2014 | Hart | G06F 3/167 |
| | | | | 704/275 |
| 2014/0334645 | A1 * | 11/2014 | Yun | G10L 15/22 |
| | | | | 381/110 |
| 2014/0365216 | A1 * | 12/2014 | Gruber | G10L 13/027 |
| | | | | 704/235 |
| 2014/0379341 | A1 * | 12/2014 | Seo | G06F 1/163 |
| | | | | 704/246 |
| 2015/0026580 | A1 * | 1/2015 | Kang | H04W 12/04 |
| | | | | 455/39 |
| 2015/0088514 | A1 * | 3/2015 | Typrin | H04M 3/493 |
| | | | | 704/231 |
| 2015/0088523 | A1 * | 3/2015 | Schuster | G10L 15/22 |
| | | | | 704/275 |
| 2015/0138333 | A1 * | 5/2015 | DeVaul | G06F 3/167 |
| | | | | 446/175 |
| 2015/0186892 | A1 * | 7/2015 | Zhang | G06Q 20/326 |
| | | | | 705/44 |
| 2015/0242932 | A1 * | 8/2015 | Beguin | G06Q 30/06 |
| | | | | 705/26.8 |
| 2015/0245154 | A1 * | 8/2015 | Dadu | G10L 19/0018 |
| | | | | 381/56 |
| 2015/0255071 | A1 * | 9/2015 | Chiba | G10L 17/22 |
| | | | | 704/275 |
| 2015/0258301 | A1 * | 9/2015 | Trivedi | A61B 5/0024 |
| | | | | 600/28 |
| 2015/0262578 | A1 * | 9/2015 | Ibuki | G10L 15/26 |
| | | | | 704/246 |
| 2015/0264432 | A1 * | 9/2015 | Cheng | H04N 21/462 |
| | | | | 725/10 |
| 2015/0378330 | A1 | 12/2015 | Xi et al. | |
| 2016/0036962 | A1 * | 2/2016 | Rand | H04M 1/656 |
| | | | | 455/418 |
| 2016/0066011 | A1 * | 3/2016 | Ro | H04M 1/72415 |
| | | | | 725/38 |
| 2016/0089028 | A1 * | 3/2016 | Chatterjee | G06F 3/011 |
| | | | | 340/870.07 |
| 2016/0117684 | A1 * | 4/2016 | Khor | H04M 3/5175 |
| | | | | 704/270 |
| 2016/0150338 | A1 * | 5/2016 | Kim | G08B 1/08 |
| | | | | 381/58 |
| 2016/0151603 | A1 * | 6/2016 | Shouldice | H04R 3/00 |
| | | | | 600/26 |

(56) References Cited

U.S. PATENT DOCUMENTS

| | | | |
|---|---|---|---|
| 2016/0154392 A1* | 6/2016 | Jo | G05B 15/02 |
| | | | 700/12 |
| 2016/0180863 A1* | 6/2016 | Ozcan | H03G 7/007 |
| | | | 381/57 |
| 2016/0260431 A1* | 9/2016 | Newendorp | G10L 15/22 |
| 2016/0260436 A1* | 9/2016 | Lemay | G10L 15/22 |
| 2016/0321506 A1* | 11/2016 | Fridental | H04N 7/181 |
| 2016/0335671 A1* | 11/2016 | Pitschel | G06Q 30/0267 |
| 2017/0032784 A1* | 2/2017 | Dadu | G06F 3/167 |
| 2017/0110124 A1* | 4/2017 | Boesen | G06F 3/04883 |
| 2017/0223482 A1* | 8/2017 | Park | G06Q 50/12 |
| 2017/0251257 A1* | 8/2017 | OBrien | H04N 21/6175 |
| 2017/0323641 A1* | 11/2017 | Shimizu | G01C 21/36 |
| 2017/0334456 A1* | 11/2017 | Deligianni | A61B 5/18 |
| 2018/0061400 A1* | 3/2018 | Carbune | G06F 16/9535 |
| 2018/0063591 A1* | 3/2018 | Newman | H04N 21/44 |
| 2018/0097837 A1 | 4/2018 | Stolarz et al. | |
| 2018/0097838 A1 | 4/2018 | Stolarz et al. | |
| 2018/0097841 A1* | 4/2018 | Stolarz | H04K 1/00 |
| 2018/0143967 A1* | 5/2018 | Anbazhagan | G06F 40/30 |
| 2018/0152557 A1* | 5/2018 | White | H04L 12/282 |
| 2018/0182389 A1* | 6/2018 | Devaraj | G10L 17/06 |
| 2018/0190264 A1* | 7/2018 | Mixter | G10L 15/22 |
| 2018/0196782 A1* | 7/2018 | Gray | G06V 40/161 |
| 2018/0204569 A1* | 7/2018 | Nadkar | G06F 3/167 |
| 2018/0268821 A1* | 9/2018 | Levanon | G10L 25/18 |
| 2018/0322893 A1* | 11/2018 | Zadgaonkar | G10L 25/66 |
| 2018/0367863 A1 | 12/2018 | Newman et al. | |
| 2019/0182176 A1* | 6/2019 | Niewczas | G10L 17/24 |
| 2019/0206399 A1* | 7/2019 | Garmark | G11B 27/11 |
| 2019/0214011 A1* | 7/2019 | Shin | G10L 21/0272 |
| 2019/0221209 A1* | 7/2019 | Bulpin | G10L 15/22 |
| 2019/0304466 A1* | 10/2019 | Xue | G10L 17/06 |
| 2019/0341026 A1* | 11/2019 | Visser | G10L 25/63 |
| 2020/0051545 A1* | 2/2020 | Iwase | G10L 25/84 |
| 2020/0117717 A1* | 4/2020 | Ramamurti | G10L 15/16 |
| 2020/0143790 A1* | 5/2020 | Trivedi | H04R 3/00 |
| 2020/0302925 A1* | 9/2020 | Shah | G06F 3/167 |
| 2020/0342855 A1* | 10/2020 | Casado | G10L 15/183 |
| 2020/0342866 A1* | 10/2020 | Casado | G06F 3/165 |
| 2020/0342881 A1* | 10/2020 | Casado | G10L 17/04 |
| 2020/0349932 A1* | 11/2020 | Ogawa | G10L 13/08 |
| 2020/0357382 A1* | 11/2020 | Ogawa | G06N 3/02 |
| 2021/0151044 A1* | 5/2021 | Yoshida | H05B 45/325 |
| 2021/0358020 A1* | 11/2021 | Yuan | G06Q 30/0641 |

OTHER PUBLICATIONS

Krejcar et al.; Use of Mobile Phones as Intelligent Sensors for Sound Input Analysis and Sleep State Detection; dated 2011.

Hossain, et al.; Finding Emotion from Multi-lingual Voice Data; dated 2020.

Lam et al.; SmartMood Toward Pervasive Mood Trackingand Analysis for Manic Episode Detection; dated 2015.

Sankaran et al.; Security over Voice Controlled Android Applications for Home IoT Systems; dated 2019.

Giannakakis et al.; Review on Psychological Stress Detection Using Biosignals; dated 2019.

Pastushenko et al.; Employment of Phase Characteristics of User Voice Signal in Authentication Systems; dated 2016.

Wang et al.; WearID Wearable-Assisted Low-Effort Authentication to Voice Assistants Using Cross-Domain Speech Similarity; dated 2020.

IP.com; Method and System for Cognitive Alarm Clock; dated 2019.

European Patent Office; International Search Report and Written Opinion of PCT Application No. PCT/US2019/061873; 14 pages; dated Jun. 23, 2020.

European Patent Office; Invitation to Pay Additional Fees; PCT Application No. PCT/US2019/061873; 13 pages; dated Mar. 10, 2020.

China National Intellecutal Property Administration; Notification of First Office Action issued in Application No. 201980043436.X; 28 pages; dated Oct. 9, 2023.

European Patent Office; Examination Report issued for Application No. 19832473.3, 8 pages, dated Jan. 24, 2024.

China National Intellecutal Property Administration; Notice of Grant issued in Application No. 201980043436.X; 4 pages; dated May 24, 2024.

* cited by examiner

CONTROLLING DEVICE OUTPUT ACCORDING TO A DETERMINED CONDITION OF A USER

BACKGROUND

Sleep quality can be pivotal to maintaining a healthy mind as one ages. Oftentimes, environmental elements that affect sleep quality can include other persons, abrupt environmental noises, and/or other subjective sensitivities that a person may have. Although there are some devices available to assist a person in falling asleep, such devices may operate inefficiently and cause incidental sleep disturbances. For instance, some white noise machines have set timers and may provide white noise at a constant level, even when a user has already fallen asleep. Should the user set the timer for a period that extends past a time they would eventually fall asleep, the white noise machine will continue providing audio at the constant level despite the user falling asleep, thereby wasting energy and computational resources. Furthermore, should the user set the timer for a period that falls short of a time when the user has initially fallen asleep, a sudden stoppage of the white noise can cause a sleep disturbance, thereby waking the user. As a result, the user may wake up and reinitialize the timer for the white noise machine, which can lead to additional energy and computational resources being expended on extending operations of the white noise machine, at least compared to a scenario where the user had remained asleep.

Similarly, a user that typically employs a computing device for playing an audiobook until they fall asleep may inadvertently cause the computing device to operate inefficiently as a result of using standard timers for stopping the audiobook once the user has fallen asleep. For instance, a user may set a timer for an audiobook to play for one hour while the user is falling asleep. Should the user fall asleep prior to the timer going off, the audiobook will continue to play at a maintained volume level until the timer going off, thereby wasting computational resources required to continue to play the audiobook at the maintained volume level. Further, the user will not comprehend a portion of the audio book should the user fall asleep prior to the timer going off. As a result, the next time the user initializes the audiobook, they would have to scroll (or otherwise navigate) through a variety of portions of the audiobook in order to identify where they left off prior to falling asleep. This can waste computational resources, as memory would be required to buffer previews of certain portions of the audiobook, and processor resources would be required to cause playback of the audiobook until the user identifies where they left off.

Other devices that operate according to whether a user is awake or asleep, such as a motion activated device, can also waste resources when an operating mode of the device is not particularly efficient in view of a state of the user. For instance, in a household where multiple people are sleeping, a single user may get up from their bed in order to have a drink of water or use the restroom. Should a motion sensor trigger a light to emit white light in response, energy required to illuminate the light may be wasted—as the user may not need a full spectrum of light to navigate from their bedroom to a kitchen or a bathroom. Furthermore, white light may be disturbing to any other person that remains asleep while the user is moving about. In some instances, such a response by a motion detector can invoke a "domino effect" of devices reacting to a presence of the user, despite the user only intending to take a small break from sleeping and return to bed. In such instances, any ancillary devices reacting to a presence of the user may inadvertently waste power and computational resources in responding to the actions taken by the user.

SUMMARY

The present disclosure is generally directed to methods, apparatus, and computer-readable media (transitory and non-transitory) for improving sleep quality for a user while simultaneously mitigating waste of computational and/or network resources. In various implementations, a condition and/or physiological attribute(s) of the user can be determined, with permission of the user, in order to determine how to effectively control one or more devices, such as an ambient noise generator and/or other computing device (e.g., a computing device devoted to automated assistant functions), to improve sleep quality for the user and/or mitigate waste of computational and/or network resources. For example, the user can have one or more assistant devices capable of responding to spoken utterances from the user, and also providing various outputs via one or more different modalities to assist a user with sleeping. The user can provide a spoken utterance such as, "Assistant, please play ambient sounds until I fall asleep." In response, and with approval of the user (e.g., previously granted approval), an automated assistant associated with the assistant devices can access data that characterizes a condition of the user and/or a previous condition of the user. For instance, the data can characterize the user as having just laid down to go to sleep immediately prior to providing the spoken utterance, and the automated assistant can, based on the data, characterize the user as being in a first condition.

The data can be based on outputs from one or more different computing devices that are in communication with the automated assistant. For instance, the data can be based on an output of a smart watch or other wearable device that the user is wearing when they are lying in their bed. The wearable device can include one or more sensors configured to be responsive to one or more different physiological attributes of the user, such as heart rate, blood pressure, oxygen level, respiratory rate, motion and/or twitch, and/or any other attribute that can indicate a condition of the person. Additionally, or alternatively, the data can be based on an output of one or more devices not being worn by the user, such as a motion sensor, a vision sensor (e.g., a camera), a standalone speaker device, a portable computing device such as, but not limited to, a tablet or cellular phone, and/or any other device capable of providing an output that indicates a condition of the user. For example, the data can be based on output from an application of a computing device, and the output can characterize a schedule of the user, thereby indicating when the user is no longer scheduled to be engaged in any certain activities.

The data can be processed to determine one or more output characteristics that would be suitable for promoting the user falling asleep. In other words, one more characteristics or settings for an output being rendered by a computing device can be identified for: reducing a probability that the user will regress away from being asleep when the user is receiving the output; and/or reducing a probability that an amount of time for the user to fall asleep will increase in response to the output having the one or more characteristics or settings when the user is receiving the output. Furthermore, the characteristics can be adjusted for any condition, including when the user is asleep or predicted to be asleep. In this way, the characteristics can continually be made suitable for ensuring the user is progressing toward falling asleep and staying asleep—at least during a period in which the user would prefer to be asleep.

For instance, when the user is in a first condition, such as, but not limited to, the user having just entered their bed to lie down, a characteristic such as volume can be selected for an ambient sound to be emitted by a computing device. When it is determined (e.g., based on a condition of the user, which can include sensed physiological attributes of the user, circumstantial attributes that can be external to the user, and/or circumstantial data that can be associated with the user) that the user is transitioning from the first condition to a second condition, such as, but not limited to, one in which the user has a higher probability of falling asleep, the characteristic can be adjusted in response. For example, a characteristic such as volume can be selected as a lower volume compared to a volume that was selected when the user was in the first condition. In this way, as the user gradually progresses closer to falling asleep or inadvertently away from staying asleep, one or more characteristics of the output being perceived by the user can be adjusted accordingly. One or more additional or alternative characteristics that can be adjusted as the user transitions towards falling asleep, or inadvertently away from staying asleep, can include equalization, reverb, tone, phase, frequency, brightness, temperature, and/or any other characteristic of an output modality that can be adjusted via a computing device.

In some implementations the user can be asleep, but regress from sleeping into a second condition. The regression can be in response to an event or environmental factor, such as wind blowing outside, traffic noises nearby, a spouse entering the home or getting up from bed, and/or any other action that can affect sleep of the user. An automated assistant, or other application or device, can identify the action as a disturbance to the user, and/or detect that the user has been disturbed, and modify one or more characteristics of the output accordingly. For example, in response to detecting a sleep disturbance, or that the user has regressed from sleep to the second condition, one or more characteristics of an output of a computing device can be adjusted in order to promote the user progressing from the second condition back to sleeping. For instance, a volume of an output can be increased in response to detecting that the user has regressed from sleeping to the second condition, thereby distorting any incidental noises that may occur when the user is in the second condition. Should the user progress from the second condition back to sleeping, the one or more characteristics can again be adjusted in order to promote the user staying asleep, or otherwise exhibiting a desired physiological attribute (e.g., exhibiting qualities of being at rest).

In some implementations, instead of requesting that ambient noise be played while the user is attempting to fall asleep, the user can request that the automated assistant stream or otherwise play other media, such as an audiobook, a podcast, a movie, a television show, etc. The media can have a finite duration, which may extend beyond an amount of time it takes for the user to transition to falling asleep. If the media continues to be rendered beyond the user falling asleep and/or continues to be rendered at the same volume and/or brightness, computational resources and/or network resources can be wasted. However, according to some implementations disclosed herein, a volume and/or brightness at which the media is rendered can be reduced responsive to determining the user is asleep. As one non-limiting example, the volume can be reduced a first amount upon determining that the user has initially fallen asleep, reduced a greater second amount upon determining that the user has progressed to a deeper state of sleep, and reduced an even greater third amount upon determining that the user has progressed to an even deeper state of sleep. Additionally or alternatively, some implementations can halt the playing of the media in response to determining the user has progressed to a certain state of sleep, or replace the rendering of the media with rendering of ambient sounds.

When the user initially lies down, the automated assistant can determine that the user is in a first condition. Data that is based on one more outputs generated when the user is in the first condition can be processed in order to determine whether the user is progressing towards a second condition, such as falling asleep or entering a near sleep state. When the user is determined to have transitioned from the first condition to the second condition, a time stamp can be identified as a temporal location within the audio data that corresponds to a time when the user entered the second condition. In this way, the user can return to the identified temporal location the following day or otherwise when they wake up, without having to search through the audiobook for a portion of the audiobook that they heard last. This can preserve computational resources, such as memory, which can be required when, absent a generated time stamp described herein, a user is previewing various portions of an audio file or an audio stream to discern what portion of the audiobook they heard last.

In some implementations, a separate timestamp can be identified in response to the user transitioning to another condition (e.g., from a near sleep state to a sleep state), despite the automated assistant already causing another timestamp to be generated. In other words, when the user transitions from the first condition to the second condition, the automated assistant can identify a first timestamp corresponding to a temporal location within some media playback when the user transitioned into the second condition. Subsequently, when the automated assistant determines that the user has transitioned from the second condition to being asleep, the automated assistant can cause the second timestamp to be identified. The second timestamp can correspond to another temporal location within the media playback at which the user transitioned from the second condition to sleeping when the media playback was being output into an environment in which the user was attempting to fall asleep. In this way, should the user subsequently want to resume playback of the media, the user can be presented with two different options, based on the two timestamps, where each option corresponds to a different temporal location of the media. For example, the user can be presented with an option to resume playback from a first location in which the user was in a near sleep state, or from a second location in which the user fell asleep.

Moreover, in some implementations disclosed herein, one more shortcuts and/or time stamps can be generated for returning to a point in the media at which the user fell asleep, entered a near sleep state, or otherwise transitioned into another condition. These shortcuts and/or time stamps can be subsequently utilized to enable a subsequent playback of the audiobook or podcast to start near or at the point in the media. As one example, the user can provide a spoken utterance to their assistant device such as, "Assistant play my audiobook." In response, the automated assistant can cause a computing device to playback and/or stream audio data corresponding to the audiobook, starting from a point in the media that corresponds to a time stamp.

In some implementations, a modality (e.g., a light source) that is different from an audio modality (e.g., a speaker) can be operated according to a detected condition of a user in order to promote a user transitioning to being, and/or staying, asleep. The modality can be, for example, a light interface, such as a display panel and/or any other source of light, which can be adjusted to provide different characteristics (e.g., frequencies, brightness, temperature, color temperature, etc.) of light according to a detected condition of the user. The detected condition can be based on determined physiological attributes of the user, and/or determined circumstantial attributes and/or circumstantial data (e.g., IoT data, schedule data, vehicle data, and/or any other data that can characterize a current and/or previous circumstance of the user) associated with the user. For instance, an automated assistant can determine that the user has been asleep for at least a threshold period of time. Subsequently, the automated assistant can determine that the user has gotten up from their bed and/or otherwise moved across a portion of an environment in which they were previously asleep. In response to determining that the user has gotten up from their bed after falling asleep, the automated assistant can cause a light source within the environment to emit a low color temperature of light. For example, initially the automated assistant can cause the light source to emit a red light at 5% of a maximum brightness capable of being output by the light source. Should the user leave the environment, for example, to use the bathroom, the automated assistant can cause the light source to reduce the brightness output to 2% or 0%. Subsequently, when the user is detected within the environment again, and a time when the user enters the environment corresponds to a time when the user is typically trying to rest, the automated assistant can cause the brightness level to increase again, back to 5%. In this way, the user can be guided by the light as they move about the environment should they wake up in the middle of the night, without wasting energy by providing all frequencies of light, such as white light, and/or providing a maximum brightness of light.

Furthermore, the light can be provided at a particular color temperature and/or brightness according to a detected condition of the user. For example, if the user is getting up from being asleep in the morning, the automated assistant can cause the light source to provide a cooler color temperature output and/or a brighter output. This can be based on an assumption that the user has slept a sufficient amount of time, and could therefore use the cooler light to help them wake up. Alternatively, or additionally, if the user is getting up from being asleep in the middle of the night, the automated assistant can cause the light source to provide a warmer color temperature output and/or a lower brightness output, relative to a brightness output that would be emitted in the morning. This can be based on an assumption that the user has not had a sufficient amount of sleep, and therefore would likely attempt to go back to sleep upon returning to their bed. In this way, energy can be preserved within the home of the user, at least because the automated assistant would cause lights to emit light according to a condition of the user, rather than merely turning on with all frequencies of light and/or full brightness whenever the user triggers the light.

In some implementations, a condition of the user can be used as a basis for providing the user with responses according to certain characteristics. In other words, one or more characteristics, for responsive outputs, can be selected in order to promote the user staying in their current condition or progressing toward falling asleep. For example, when the user is determined to be asleep, but nonetheless unexpectedly provides a spoken utterance such as, "Assistant, turn on the lights," the automated assistant can cause the lights to turn on—but according to characteristics selected for the user being asleep. Specifically, the characteristics can include, for example, a 5% dimming level and/or a low color temperature (e.g., a red light). In some implementations, when the user is determined to be in a second condition, such as, but not limited to, just before the user falls asleep, and provides a spoken utterance such as, "Assistant, what time is it," the automated assistant can provide an audible response according to characteristics selected for the second condition. For instance, the audible response can be provided at a lower volume compared to a volume that would otherwise be selected if the user was awake and/or in a second condition, such as, but not limited to, when the user is determined to be in a sleep state. In this way, various modalities of a computing device and/or a peripheral device can be controlled according to a determined condition (e.g., physiological attribute(s) of the user and/or circumstantial attribute(s) of the user).

In some implementations, when an automated assistant device is invoked, responsive to an invocation phrase (e.g., "Hey, Assistant") or otherwise (e.g., responsive to a gesture), the automated assistant device can acknowledge that it has been invoked by rendering an ambient sound (e.g., birds chirping, ocean waves, waterfall, and/or any other suitable ambient sound). The ambient sound can optionally continue to be rendered so long as the automated assistant device is invoked. For example, the ambient sound can continue to be rendered so long as the automated assistant device is performing certain processing of captured audio that is only performed when invoked, such as transmission of the captured audio to a remote server for speech-to-text processing, or local speech-to-text processing. In other words, instead of, or in addition to, the automated assistant device illuminating an LED or providing other visual output to indicate it has been invoked, the automated assistant device can provide ambient noise or other sounds to indicate it has been invoked—and optionally to indicate it continues to be invoked. This can be beneficial in various scenarios, such as when a user is attempting to sleep and has his/her eyes shut, when the automated assistant device is not visible to the user, the user is visually impaired, etc. In some implementations, the sound that is rendered by the automated assistant device when invoked, can optionally be rendered in a manner that is based on sensed physiological attributes of the user and/or determined circumstantial attributes of the user. For example, if the user is in a near sleep state, the sound can be rendered at a first volume whereas if the user is in an awake state, the sound can be rendered at a second louder volume.

In some implementations, the sound that is rendered by the automated assistant device when invoked, can optionally be rendered according to a voice signature and/or voice identification of the user. For instance, when a first user provides an invocation phrase such as, "Assistant," the automated assistant device can respond by playing a sound of birds chirping in order to indicate to the first user that the automated assistant device is anticipating a spoken utterance from the first user. Additionally, when a second user provides the invocation phrase, the automated assistant device can respond by playing a sound of ocean waves in order to indicate that the automated assistant is anticipating a spoken utterance from the second user. Additionally, or alternatively, the sound that is rendered by the automated assistant device when invoked, can optionally be rendered based on detected ambient sound, background noise, a distance of a user from the automated assistant device, and/or any other indicators that can be associated with sleep state of a user. For instance, in some implementations a sound rendered, specifically for responding to the first user or the second user, can have one or more characteristics that can be modified according to detected ambient sound, background noise, a distance of a user from the automated assistant device, and/or any other indicators that can be associated with sleep state of a user. For example, one or more values of characteristics such as volume, equalization, tone, reverb, delay, and/or any other sound feature can be adjusted. In this way, should the first user attempt to invoke the automated assistant when there is some amount of detected background noise, the sound of birds chirping can have a volume value that is based on a volume of the detected background noise.

The above description is provided as an overview of some implementations of the present disclosure. Further description of those implementations, and other implementations, are described in more detail below.

Other implementations may include a non-transitory computer readable storage medium storing instructions executable by one or more processors (e.g., central processing unit(s) (CPU(s)), graphics processing unit(s) (GPU(s)), and/or tensor processing unit(s) (TPU(s)) to perform a method such as one or more of the methods described above and/or elsewhere herein. Yet other implementations may include a system of one or more computers and/or one or more robots that include one or more processors operable to execute stored instructions to perform a method such as one or more of the methods described above and/or elsewhere herein.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1A:
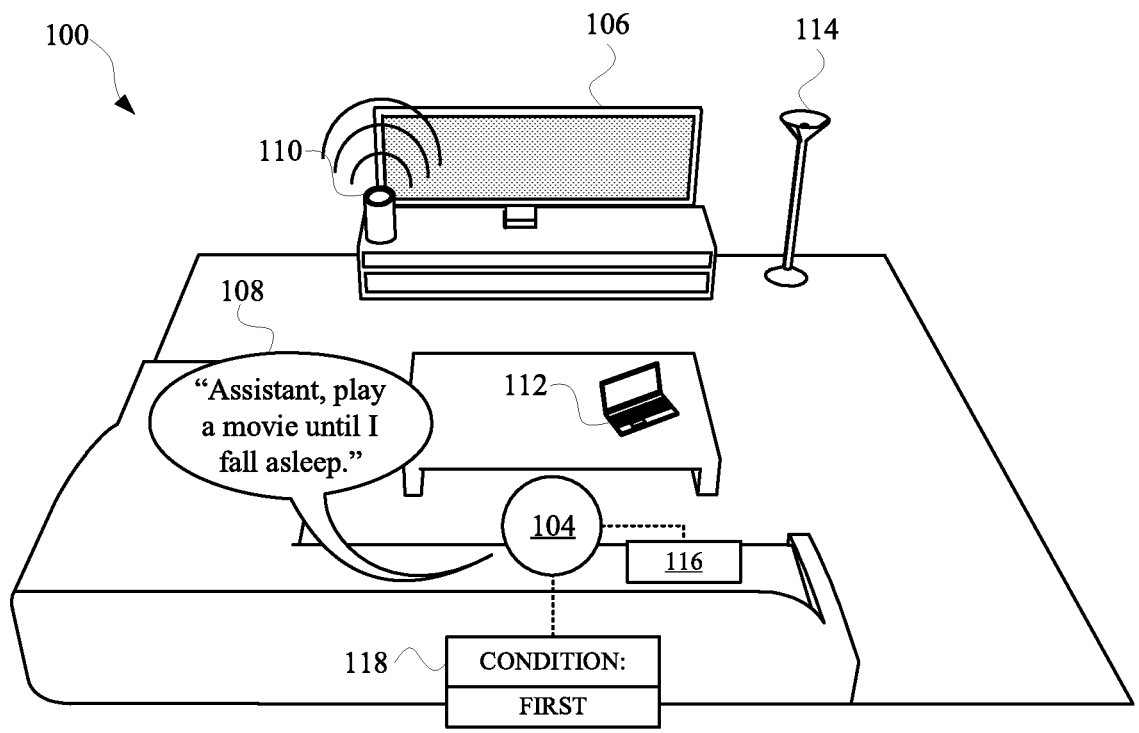
FIG. 1A and FIG. 1B illustrates perspective view of a first computing device modifying a particular output according to a condition of a user.
Figure 1B:
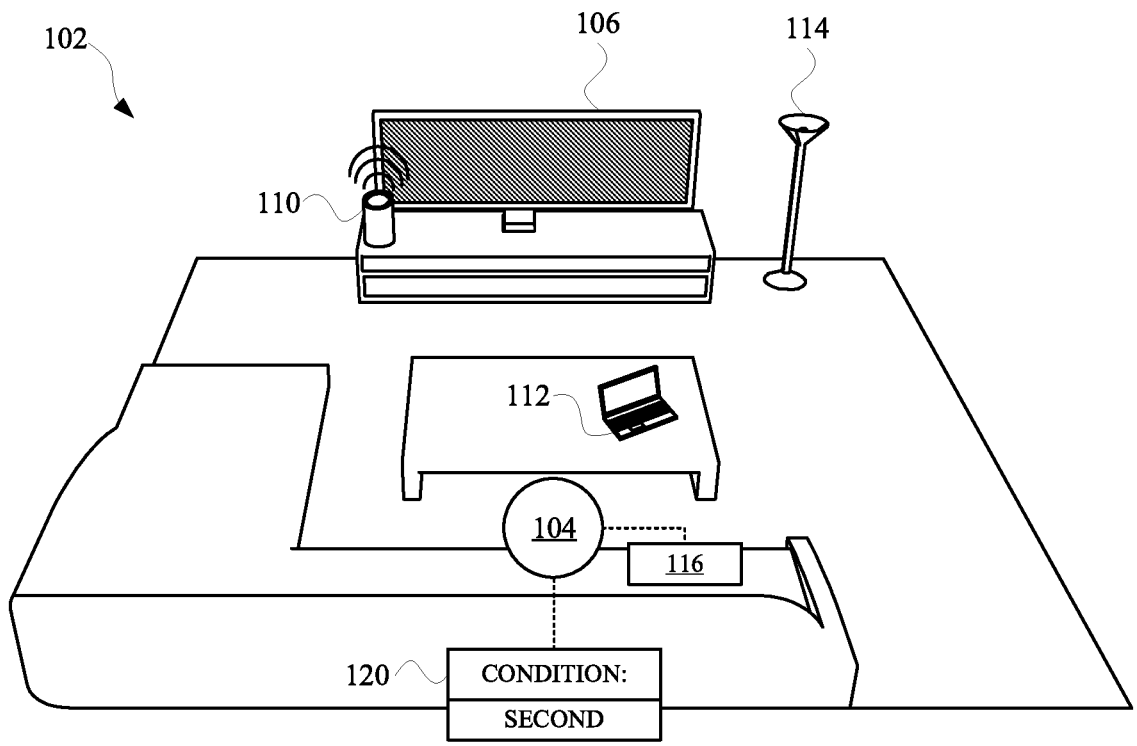

FIG. 1A and FIG. 1B illustrates perspective view 100 and a perspective view 102, respectively, of a first computing device 106 modifying a particular output according to a condition of a user 104. Specifically, as the first computing device 106 determines that the user 104 is progressing toward a sleep state, the first computing device 106 can modify one or more characteristics of the output in order to promote or encourage the user 104 progressing toward the sleep state and/or staying in the sleep state. Initially, the user 104 can be watching a movie via the first computing device 106, as illustrated in FIG. 1A. The user 104 can request that the first computing device 106 play the movie until the user 104 falls asleep by providing a spoken utterance 108 requesting that the movie be played until the user 104 falls asleep. For instance, the user 104 can provide a spoken utterance 108, such as, "Assistant, play a movie until I fall asleep," to a second computing device 110, which can be, for example, a standalone-speaker device or other assistant-enabled device. In response, an automated assistant can process the spoken utterance 108 and cause the first computing device 106 to play the movie accordingly.

The automated assistant can access data for determining a particular condition of the user 104. Permission to access such data can be provided by the user 104 and subsequently inferred from the spoken utterance 108 in which the user 104 requested playback of the movie until the user 104 falls asleep. The data can be provided from one or more sources such as the first computing device 106, the second computing device 110, a third computing device 112 (e.g., a laptop or other portable computing device), one or more server devices, and/or any apparatus or application capable of providing data. For instance, the data can be at least in part generated based on an output of a lighting device 114, which can be connected to the first computing device 106 over a local area network, such as a Wi-Fi network. The lighting device 114 can include one or more sensors, such as a motion sensor, and the data can therefore be based on an output of the motion sensor. When the automated assistant receives the spoken utterance 108 from the user 104, the automated assistant can access the data and determine that the user 104 has transitioned from a first condition to a second condition, at least based on the data indicating a decrease in an amount of movement of the user 104.

In response to determining that the user 104 has transitioned from the first condition to the second condition, the first computing device 106 can cause one or more changes to one or more characteristics of an output being provided by the first computing device 106. For instance, a characteristic that can be changed in response to determining that the user 104 transitioned from the first condition to the second condition can include audio volume, brightness of light, temperature of light, number of active speakers, equalization of sound, frequency of light and/or sound, and/or any other characteristic of an output of a computing device.

In some implementations, the automated assistant and/or the first computing device 106 can access additional data for determining whether the user 104 has transitioned from the second condition to the sleep state. The additional data can be generated based on an output from one or more different devices, such as a wearable device 116 being worn by the user 104 and/or the lighting device 114. For example, the wearable device 116 can be a watch that includes one or more sensors that are responsive to changes in physiological features of the user 104. The sensors of the wearable device 116 can include a heart rate sensor, blood pressure sensor, blood-oxygen sensor, respiratory rate sensor, temperature sensor, motion sensor, tactile sensor, and/or any other sensor capable of being responsive to a particular condition and/or action of the user 104. When the user 104 is determined to be in the sleep state, at least based on processing the additional data, the first computing device 106 can cause one or more changes to one or more characteristics of the output being provided by the first computing device 106. For instance, a characteristic that can be modified in response to determining that the user 104 entered the sleep state can be volume, brightness, frequency, temperature of light, frequency, equalization, and/or any other characteristic discussed herein.

In some implementations, one or more characteristics of the output of the first computing device 106 can be changed and, additionally, the output can be modified according to a sleep state protocol. For example, when the automated assistant and/or the first computing device 106 determines that the user 104 has entered the sleep state, the first computing device 106 can be caused to modify the output according to a sleep state protocol. The sleep state protocol can be directed at controlling the output to encourage the user 104 to stay in the sleep state and, therefore, minimize abrupt changes in output and/or otherwise reduce a probability that the user will regress from the sleep state to the second condition and/or the first condition. For instance, the automated assistant and/or the first computing device 106 can determined, based on the additional data, that the user 104 may remain in the sleep state as long as some amount of ambient noise is being provided by the first computing device 106 and/or the second computing device 110. This determination can be based on historical responsiveness of the user 104 to the ambient noise, as detected by the automated assistant. Therefore, when the user 104 enters the sleep state, or during a time subsequent to the user 104 entering the sleep state, the automated assistant can cause the first computing device 106 and/or the second computing device 110 stop playing the output (e.g., the movie) and provide a different output, such as ambient noise. In this way, one or more devices can be responsive to the user transitioning between sleep states.

Figure 2A:
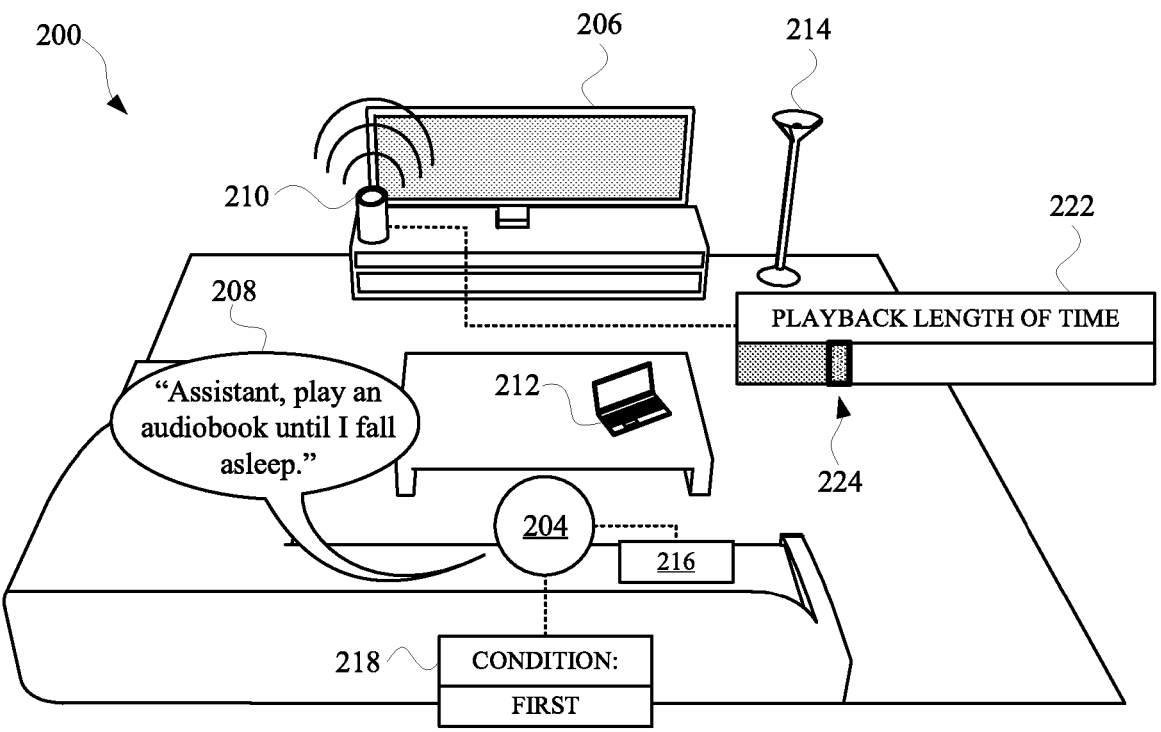
FIG. 2A and FIG. 2B illustrate perspective views of one or more timestamps being generated according to a condition of a user when the user is listening to, or otherwise perceiving, an output of a computing device.
Figure 2B:
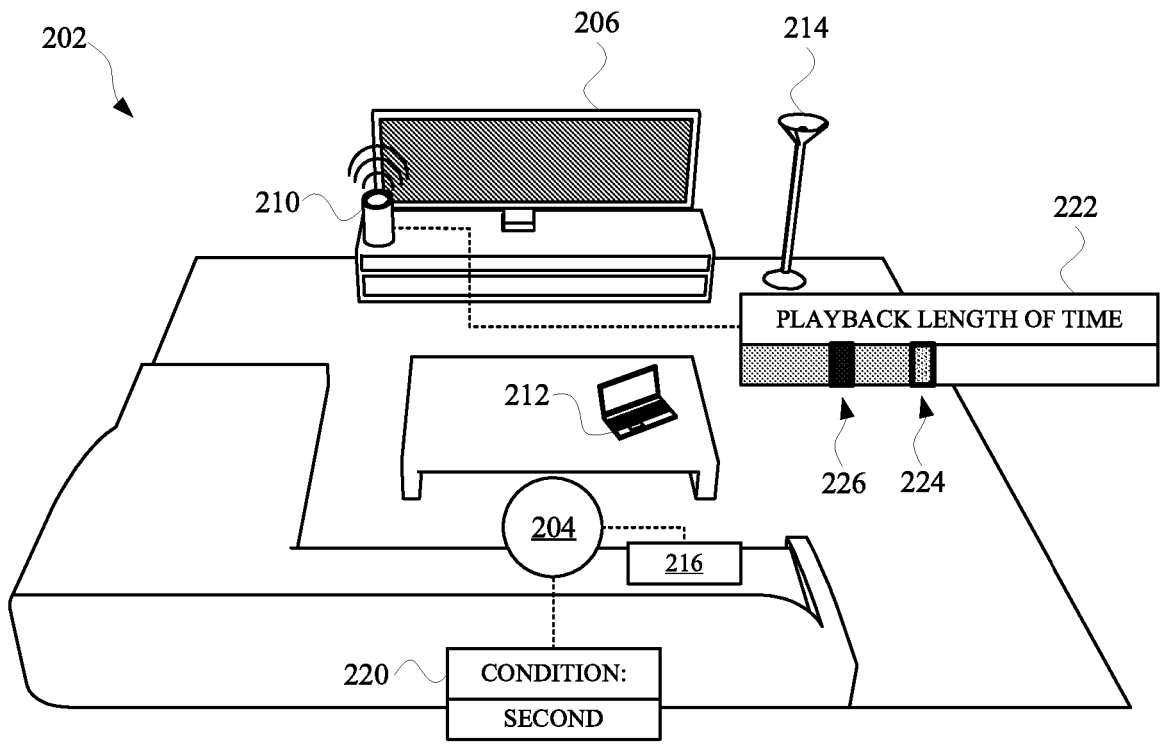

FIG. 2A and FIG. 2B illustrate perspective view 200 and perspective view 202, respectively, of one or more timestamps being generated according to a condition of a user 204, when the user 204 is listening to, or otherwise perceiving, an output of a computing device. For instance, the user 204 can request that either a first computing device 206 and/or a second computing device 210 provide a particular output (e.g., audio and/or video output) by speaking a spoken utterance 208 such as, "Assistant, play an audiobook until I fall asleep." In response to an automated assistant, accessible via the second computing device 210, receiving the spoken utterance 208, the automated assistant can cause the second computing device 210 to provide an output. The output can be, for example, audio corresponding to an audiobook having a finite length of time, which can be symbolized by an element 222, which also characterizes a temporal position 224 within the length of time that the user 204. The temporal position 224 can identify a portion of an audio file that the user 204 is currently perceiving. For example, if the user 204 has listened to a quarter of an audiobook that is characterized by an audio file having a length of an hour, the next time the user 204 initializes the audiobook for listening, the audiobook can begin at the temporal position 224 corresponding to 15 minutes from the beginning audio file.

Initially, when the user 204 provides the spoken utterance 208, the automated assistant can receive the spoken utterance 208 and, in response and with previously granted permission from the user 204, determine a condition of the user. The condition of the user 204 can characterize, or be based on, one or more physiological features of the user 204. For instance, a third computing device 212 can indicate an amount of interaction that has been occurring between the user 204 and the third computing device 212. Additionally, or alternatively, the third computing device 212 and/or any other source of data can characterize a schedule of the user 204, thereby providing information from which to predict when the user 204 may desire to fall asleep, or at least be exhibiting a restful state.

Initially, the user 204 can be determined to be in a first condition 218, based on data from one or more sources. The user 204 can be determined to be in the first condition 218 by the automated assistant, which can cause data from one or more sources to be processed for determining whether the data satisfies one or more conditions for identifying whether the user 204 is in the first condition 218 and/or is otherwise exhibiting physiological attributes corresponding to the first condition 218. In some implementations, the user 204 can be determined to be in the first condition based on the user 204 at least requesting that the automated assistant provide some amount of media playback (e.g., an audiobook or other media) that has a playback length of time (e.g., corresponding to element 222) estimated to extend into a time period (e.g., 11 PM to 6:30 AM) when the user 204 is asleep. Initially, playback can begin at a temporal position 224, which is depicted graphically in FIG. 2A.

Eventually, the user 204 can continue comprehending and/or perceiving the media while the user 204 simultaneously transitions into a second condition 220. When the user 204 is determined to have transitioned from the first condition to the second condition, the automated assistant and/or the first computing device 206 can cause a time stamp 226 to be generated. The time stamp can identify a temporal location within a length of time of the media (e.g., audiobook, music, movie, and/or other file being played back by the first computing device 206 and/or second computing device 210) corresponding to a time at which the user 204 transitioned from the first condition to the second condition. In other words, as the user 204 is perceiving an output from the first computing device 206 and/or the second computing device 210, the user 204 can transition to the second condition at a point in time of playback of the output, and the time stamp 226 can characterize that point in time. In this way, the user 204 can quickly navigate to that point, within the media data (e.g., a file, stream, and/or other source of data), corresponding to a time that the user 204 transitioned into the second condition. This can preserve computational resources, as the user 204 would spend less time previewing different portions of the file, thereby causing less previews to be cached in memory.

In some implementations, when the user 204 is determined to have transitioned from the first condition 218 to the second condition 220, and/or the second condition 220 to a desired condition in which the user 204 is exhibiting one or more particular physiological attributes, the output being provided to the user 204 can be caused to change. For instance, when the user 204 is determined to have transitioned to the second condition, or another desired condition or state (e.g., a sleep state), the media playback can transition from being based on a first source of data (e.g., a file or stream of an audiobook) to a second source of data (e.g., a file or stream of ambient sound). In this way, disruptions to a condition and/or state of the user 204 can be eliminated by mitigating disruptive endings to particular outputs.

Additionally, or alternatively, when the output provided by the first computing device 206 is a visual output and the user 204 is in the first condition 218, the visual output can be modified in response to determining that the user 204 is in the second condition 220. For instance, as illustrated in FIG. 2A and FIG. 2B, when the user transitions from the first condition 218 to the second condition 220, the first computing device 206 can alter a level of brightness of the first computing device 206 in response. Alternatively, or additionally, when the user is determined to have transitioned from the first condition to the second condition, a visual output of the first computing device 206 can be modified by adjusting one or more characteristics including, but not limited to, brightness, color, color temperature, refresh rate, display size, bitrate, frame rate, gamma, bits per second, and/or any other characteristic of a computer-generated visual output. Changes to such characteristics as the user transitions between conditions can be learned over time and adapted, in order to promote the user falling asleep without interruption and/or otherwise exhibit one or more attributes (e.g., physical attributes associated with relaxation).

Figure 3A:
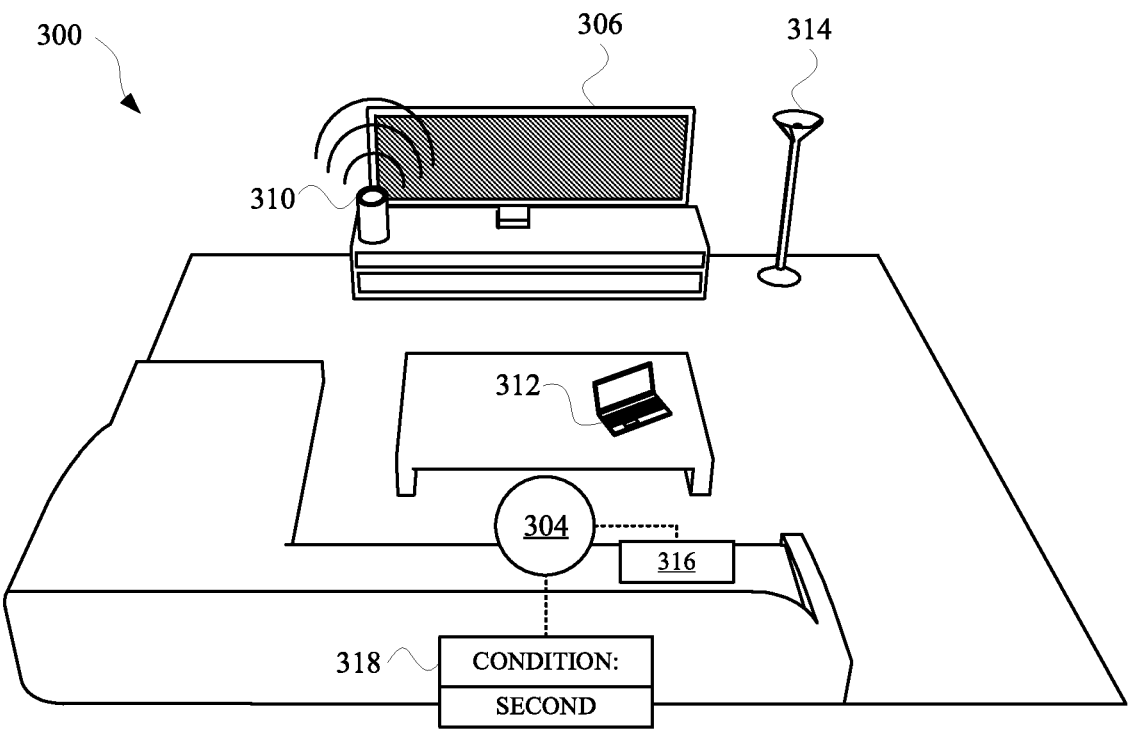
FIG. 3A and FIG. 3B illustrate views of implementations wherein one or more output of one or more computing devices can be modified in response to a user regressing from a sleep state or other desired physiological state, to a different state.
Figure 3B:
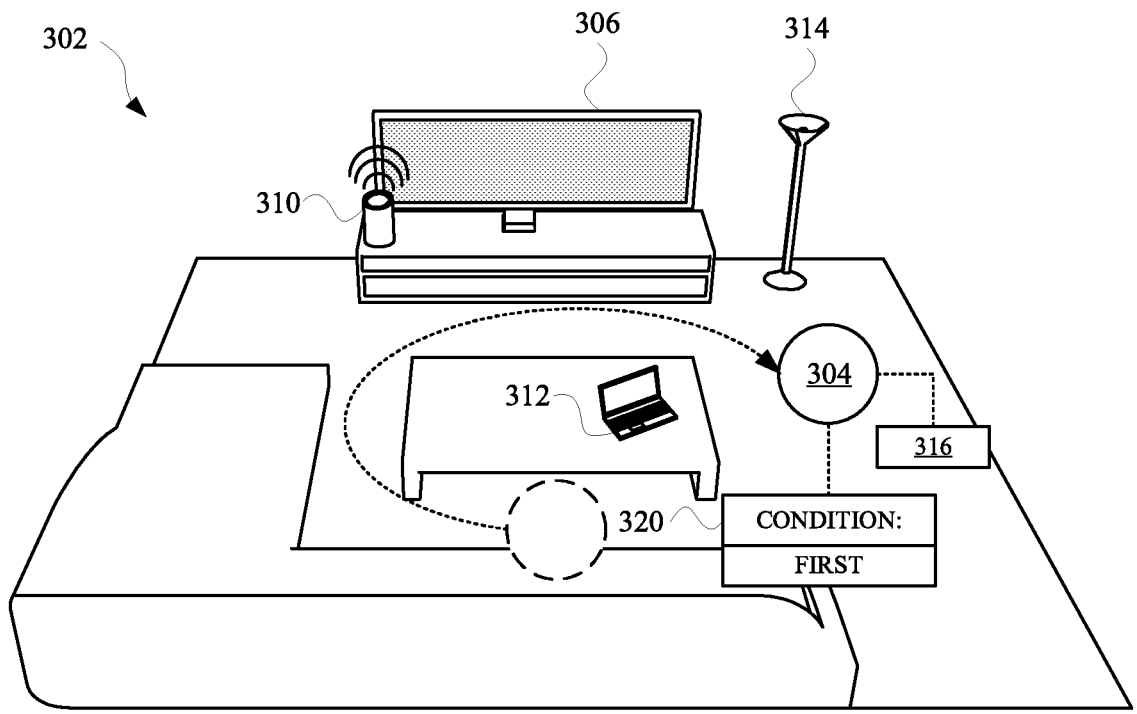

FIG. 3A and FIG. 3B illustrate view 300 and 302, respectively, of implementations wherein one or more outputs of one or more computing devices can be modified in response to a user 304 regressing from a sleep state or other desired physiological state, to a different state. For instance, the user 304 can be determined to be in a sleep state or second condition 318, in furtherance of staying asleep or otherwise staying in that particular physiological state, such as a relaxed state. While the user is in the second condition, a first computing device 306 can be off or otherwise providing a limited output compared to if the user was awake. Alternatively, or additionally, a second computing device 310 can be playing back ambient noise in order to encourage the user 304 staying in the second condition 318 or sleep state. Furthermore, a lighting device 314 can be located within the environment, such as a living room, of the user 304, but can be in an off state when the user is in the second condition 318. This configuration of devices, settings, and/or characteristics, can be controlled by the automated assistant and selected based on the condition of the user 304, and with permission from the user 304.

When the automated assistant, and/or another application or device, determines that the user has transitioned from the second condition to the first condition 320, configurations of one or more devices can be modified in response. For instance, in response to the user 304 transitioning from the second condition 318 to the first condition 320, the automated assistant can cause the lighting device 314 to emit light according to one or more characteristics. Specifically, the characteristics can be selected according to the condition of the user. For instance, based on the user transitioning from the second condition to the first condition, the automated assistant can cause a particular color and/or color temperature of light to be emitted by the lighting device 314. As an example, the lighting device 314 can provide a red color of light and a brightness level that is 5% of a maximum brightness level that is capable of being emitted by the lighting device 314. In this way, the automated assistant can adapt the one or more characteristics according to a current condition of user and/or a previous condition of the user.

Alternatively, or additionally, circumstantial data can be used in combination with a determined condition of the user 304 to identify the one or more characteristics for modifying outputs of devices within the environment. For example, a time of day and/or an amount of time that the user has been in the second condition 318 can be used to determine whether to cause the lighting device 314 to emit red light or blue light. Specifically, the automated assistant can cause the lighting device 314 to emit red light when the user 304 has been in the second condition for less than a threshold period of time and/or a current time of day is within a night-time range (e.g., 10 p.m. to 4 a.m.). However, the automated assistant can also cause the lighting device 314 to emit blue light when the user has been in a second condition for equal to, or greater than, a threshold period of time and/or a current time of day is within a morning or day time range (e.g., 4 a.m. to 10 p.m.). In this way, each output can be adapted to encourage the user to stay asleep in some conditions, and/or motivate the user to stay awake in other conditions, according to a preference of the user 304.

In some implementations, adapting characteristics when the user regresses from the second condition to the first condition 320 can be performed for outputs of the first computing device 306, the second computing device 310, and/or the third computing device 312. For instance, in response to the user 304 regressing from the second condition 318 to the first condition 320, the first computing device 306 can provide a brighter light output. Alternatively, or additionally, in response to the user regressing from the second condition 318 to the first condition 320, the second computing device can provide a higher amplitude audio output relative to the audio output being provided when the user was in the second condition 318. Furthermore, an automated assistant accessible via the third computing device 312 can provide ambient noise when invoked by the user 304 when the user is within the second condition 318. Additionally, the automated assistant accessible via the third computing device 312 can provide light and/or a natural language output when invoked by the user 304 when the user 304 is within the first condition 320.

Figure 4:
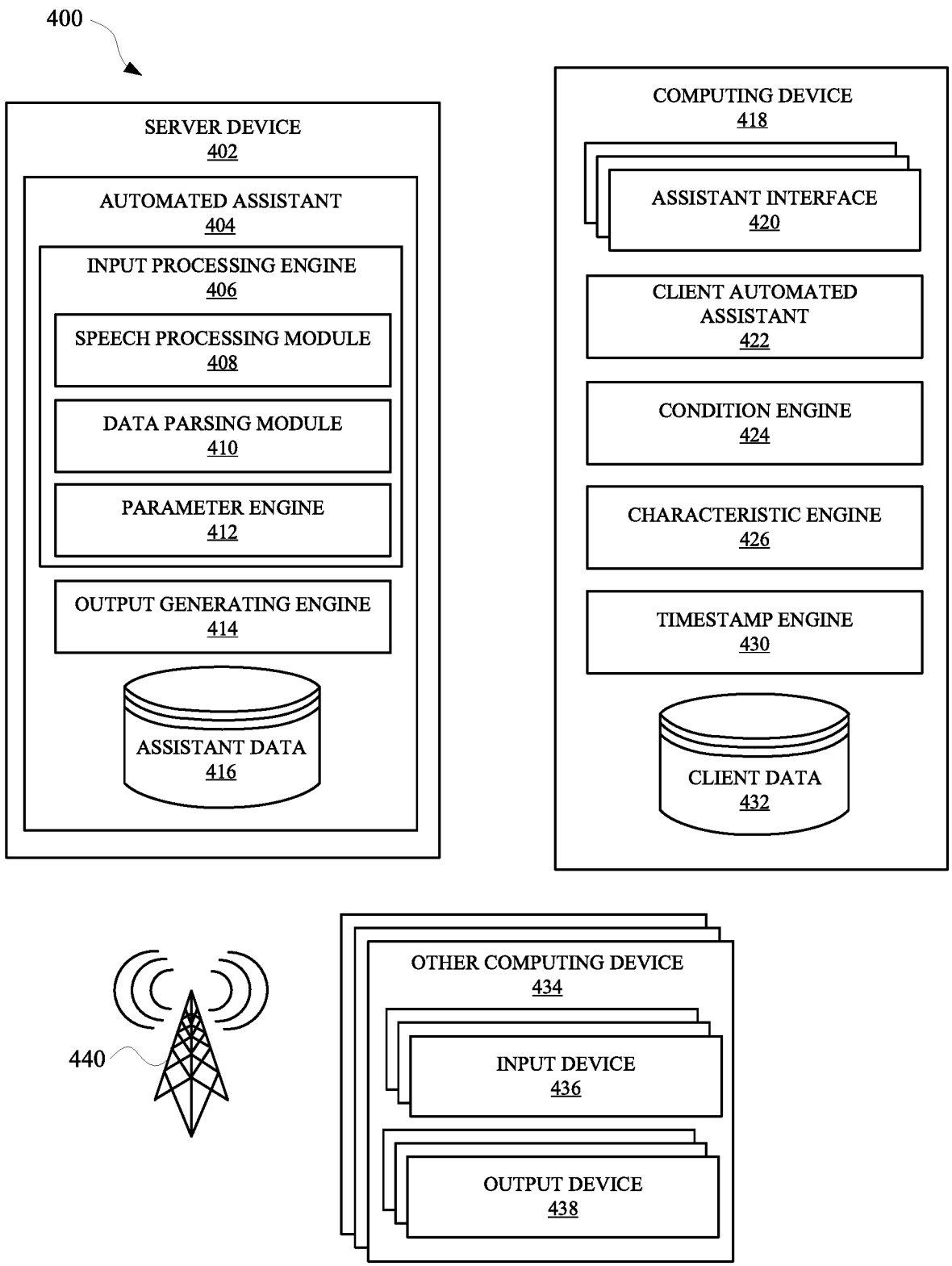
FIG. 4 illustrates a system for modifying one or more characteristics of an output of a computing device and/or automated assistant according to a condition of a user, for example, in order to assist the user with falling asleep.

FIG. 4 illustrates a system 400 for modifying one or more characteristics of an output of a computing device and/or automated assistant 404 according to a condition of a user, for example, in order to assist the user with falling asleep. The automated assistant 404 can operate as part of an assistant application that is provided at one or more computing devices, such as a computing device 418 and/or a server device 402. A user can interact with the automated assistant 404 via an assistant interface, which can be a microphone, a camera, a touch screen display, a user interface, and/or any other apparatus capable of providing an interface between a user and an application. For instance, a user can initialize the automated assistant 404 by providing a verbal, textual, or a graphical input to the assistant interface to cause the automated assistant 404 to perform a function (e.g., provide data, control a peripheral device, access an agent, generate an input and/or an output, etc.). The computing device 418 can include a display device, which can be a display panel that includes a touch interface for receiving touch inputs and/or gestures for allowing a user to control applications of the computing device 418 via the touch interface. In some implementations, computing device 418 can lack a display device, thereby providing an audible user interface output, without providing a graphical user interface output. Furthermore, the computing device 418 can provide a user interface, such as a microphone, for receiving spoken natural language inputs from a user. In some implementations, the computing device 418 can include a touch interface and can be void of a camera, but can optionally include one or more other sensors.

The computing device 418 and/or other computing devices 434 can be in communication with the server device 402 over a network 440, such as the internet. Additionally, the computing device 418 and the other computing devices 434 can be in communication with each other over a local area network (LAN), such as a WiFi network. The computing device 418 can offload computational tasks to the server device 402 in order to conserve computational resources at the computing device 418. For instance, the server device 402 can host the automated assistant 404, and computing device 418 can transmit inputs received at one or more assistant interfaces 420 to the server device 402. However, in some implementations, the automated assistant 404 can be hosted at the computing device 418 as a client automated assistant 418.

In various implementations, all or less than all aspects of the automated assistant 404 can be implemented on the computing device 418. In some of those implementations, aspects of the automated assistant 404 are implemented via the client automated assistant 422 of the computing device 418 and interface with the server device 402 that implements other aspects of the automated assistant 404. The server device 402 can optionally serve a plurality of users and their associated assistant applications via multiple threads. In implementations where all or less than all aspects of the automated assistant 404 are implemented via a client automated assistant 422 at the computing device 418, the client automated assistant 422 can be an application that is separate from an operating system of the computing device 418 (e.g., installed "on top" of the operating system)—or can alternatively be implemented directly by the operating system of the computing device 418 (e.g., considered an application of, but integral with, the operating system).

In some implementations, the automated assistant 404 and/or the client automated assistant 422 can include an input processing engine 406, which can employ multiple different modules for processing inputs and/or outputs for the computing device 418 and/or the server device 402. For instance, the input processing engine 406 can include a speech processing module 408 that can process audio data received at an assistant interface 420 to identify the text embodied in the audio data. The audio data can be transmitted from, for example, the computing device 418 to the server device 402 in order to preserve computational resources at the computing device 418.

The process for converting the audio data to text can include a speech recognition algorithm, which can employ neural networks, word2vec algorithms, and/or statistical models for identifying groups of audio data corresponding to words or phrases. The text converted from the audio data can parsed by a data parsing module 410 and made available to the automated assistant as textual data that can be used to generate and/or identify command phrases from the user. In some implementations, output data provided by the data parsing module 410 can be provided to a parameter module 412 to determine whether the user provided an input that corresponds to a particular action and/or routine capable of being performed by the automated assistant 404 and/or an application or agent that is capable of being accessed by the automated assistant 404. For example, assistant data 416 can be stored at the server device 402 and/or the computing device 418, as client data 432, and can include data that defines one or more actions capable of being performed by the automated assistant 404 and/or client automated assistant 422, as well as parameters necessary to perform the actions.

In some implementations, the other computing device 434 can receive inputs from the computing device 418 and/or the server device 402, and provide outputs for the user, and/or transmit outputs to the computing device 418 and/or the server device 402. For instance, the user can provide a request for the client automated assistant 422 to provide an output for assisting the user with falling asleep. The request can be embodied as a spoken utterance such as, "Assistant, play my television series until I fall asleep." In response, audio data corresponding to the spoken utterance can be provided to the server device 402 and processed by the input processing engine 406. The input processing engine 406 can identify the television series that the user is referring to, and cause the computing device 418 and/or another computing device 434 to provide an audio-visual output corresponding to the television series.

Furthermore, and in some implementations, the computing device 418 and/or the server device 402 can include a condition engine 424. The condition engine 424 can determine and/or characterize a circumstance in which an automated assistant received a request. The circumstance can be characterized based on one or more sources of data, such as data from the computing device 418, data from the server device 402, and/or data from one or more other computing devices 434. In some implementations, the other computing devices 434 can include a wearable device, a portable computing device, a vehicle, a robotic device, and/or any other computing device capable of providing data to another computing device. One or more other computing devices 434 can include one or more input devices 436 and/or one or more output devices 438. For instance, the one or more input devices 436 can include one or more sensors, interfaces, processors, memory devices, receivers, and/or any other apparatus capable of receiving an input. Furthermore, the one or more output devices 438 can include one or more interfaces such as a speaker, a display panel, a light, a motor, and/or any other apparatus that can receive a signal from a computing device.

When the other computing devices 434 include a wearable device, the condition engine 424 can determine the condition of the user and/or the request provided by the user based on data generated based on one or more input devices for 436 of the wearable device. For example, the wearable device can include one or more sensors capable of being responsive to changes in physiological attributes of the user. Data characterizing the physiological attributes of the user can be transmitted from the other computing device 434 to the condition engine 424 in order to determine a condition of the user. The condition engine 424 can determine, for example, that the user is in a first condition, and has therefore initialized actions in furtherance of falling asleep. The determination of the condition can then be communicated by the condition engine 424 to the characteristic engine 426.

The characteristic engine 426 can identify one or more characteristics of one or more outputs to adapt according to the condition determined by the condition engine 424 and/or the request or action to be performed for the user. For instance, when the user is determined to have requested a television series to be output, the characteristic engine 426 can determine based on the condition, and/or the request, one or more characteristics of the output to modify. In some implementations, a characteristic of an audio portion of the output can be modified, and another characteristic of a visual portion of the output can be modified according to the condition of the user. Specifically, as an example, a volume of the audio portion of the output can be adjusted to be lower relative to a previous volume of the audio portion of the output when the user previously requested the output be provided. Furthermore, as an example, a color temperature of the visual portion of the output can be warmer, or include less blue light, relative to a previous color temperature of the visual portion of the output when the user previously requested the output be provided.

Additional data can be transmitted to the condition engine 424 for determining whether the user has transitioned out of the first condition. For instance, the server device 402, the other computing device 434, and/or the computing device 418 can generate data from which the condition engine 424 can determine the condition of the user. In some implementations, when the user is determined to have transitioned from the first condition to a second condition, a timestamp engine 430 can identify a temporal location within an output of the computing device 418, or another computing device 434, in which to direct or assign a particular time stamp. Furthermore, in some implementations, when the user is determined to have transitioned from the second condition to a sleep state, or has otherwise been determined to have fallen asleep, the timestamp engine 430 can identify another temporal location within the output of the computing device 418 at which to direct or assign another particular time stamp. In this way, should the user fall asleep during playback of a media source, the user can easily identify a location where they may have fallen asleep or otherwise been inattentive to the media. In some implementations, the timestamp engine 430 can generate a timestamp based on a predicted time at which the user will transition between conditions and/or physiological states. Such a predicted time can be based on historical data (e.g., stored as client data 424 and/or assistant data 416) that characterizes times at which the user typically transitions between conditions, such as when the user falls asleep.

In some implementations, the automated assistant 404, and/or the client automated assistant 422 can respond to spoken utterances, such as an invocation phrase, from the user based on a determined condition of the user. For example, when the condition engine 424 determines that the user is in a second condition, the client automated assistant 422 can operate according to a setting wherein an assistant interface 420, such as a speaker, will output ambient noise in response to an invocation phrase such as, "Assistant . . ." Furthermore, one or more characteristics of the responsive output from the automated assistant can be based on the condition, the user, and/or any other information that can provide a basis for modifying an output of a device. For instance, the automated assistant can determine that user provided the invocation phrase, identify a particular ambient noise selected by, or assigned to, the user, and cause the particular ambient noise to be output by the computing device 418. Should a different user provide the invocation phrase, the automated assistant can identify the different user, identify a different ambient noise selected by, or assigned to, the different user, and cause the different ambient noise to be output by the computing device 418. Additionally, or alternatively, characteristics of the responsive output can be adjusted according to the condition, the user, and/or any other information.

For instance, when the responsive output is a light output, a property of light, such as temperature and/or brightness, can be selected according to the condition, the user, and/or any other information. For example, when the first user provides an invocation price, a first pattern of light can be emitted in response, and when a second user provides the invocation phrase, a second pattern of light, which is different than the first pattern of light, can be emitted in response. The responsive output can be an indication that the automated assistant has acknowledged the invocation phrase and/or is awaiting further instructions from the user. By providing a responsive output that is not a natural language output, such as, "How can I help you?" the user will be less disturbed by the output, should the user be attempting to fall asleep when the user provided the invocation phrase. Furthermore, such responsive output can mitigate the chance of the automated assistant waking up other users within the environment or home in which the user provided the invocation phrase.

In some implementations, the system 400 can be responsive to a user regressing away from a sleep state, or otherwise transitioning out of a particular condition. For instance, when the user awakens from a sleep state, the automated assistant can determine a condition of the user when the user awakens and/or immediately before the user wakes up. Depending on what the user is attempting to do when they wake up, the automated assistant and/or one or more other computing devices 434 can respond accordingly. For instance, when the condition engine 424 determines based on additional data that the user has been in a sleep state for less than a threshold period of time and has awakened, the condition engine 424 can communicate the condition to the characteristic engine 426. The characteristic engine 426 can modify an output of another computing device 434 to provide a light output, such as a red light output, in order to illuminate a path for the user while also providing less stimulating light for preventing further awakening the user. Alternatively, when the condition engine 424 determines, based on additional data, that the user has been in a sleep state for at least a threshold period of time and woken up, the condition engine 424 can communicate this condition to the characteristic engine 426. The characteristic engine can then modify an output of another computing device 434 to provide a light output, such as a blue light output, in order to illuminate a path for the user and also provide some amount of stimuli that would assist the user in waking up. In some implementations, the threshold period of can be dynamic and/or adjusted according to sleep habits of the user and/or preferences of the user learned over time by the automated assistant.

Figure 5:
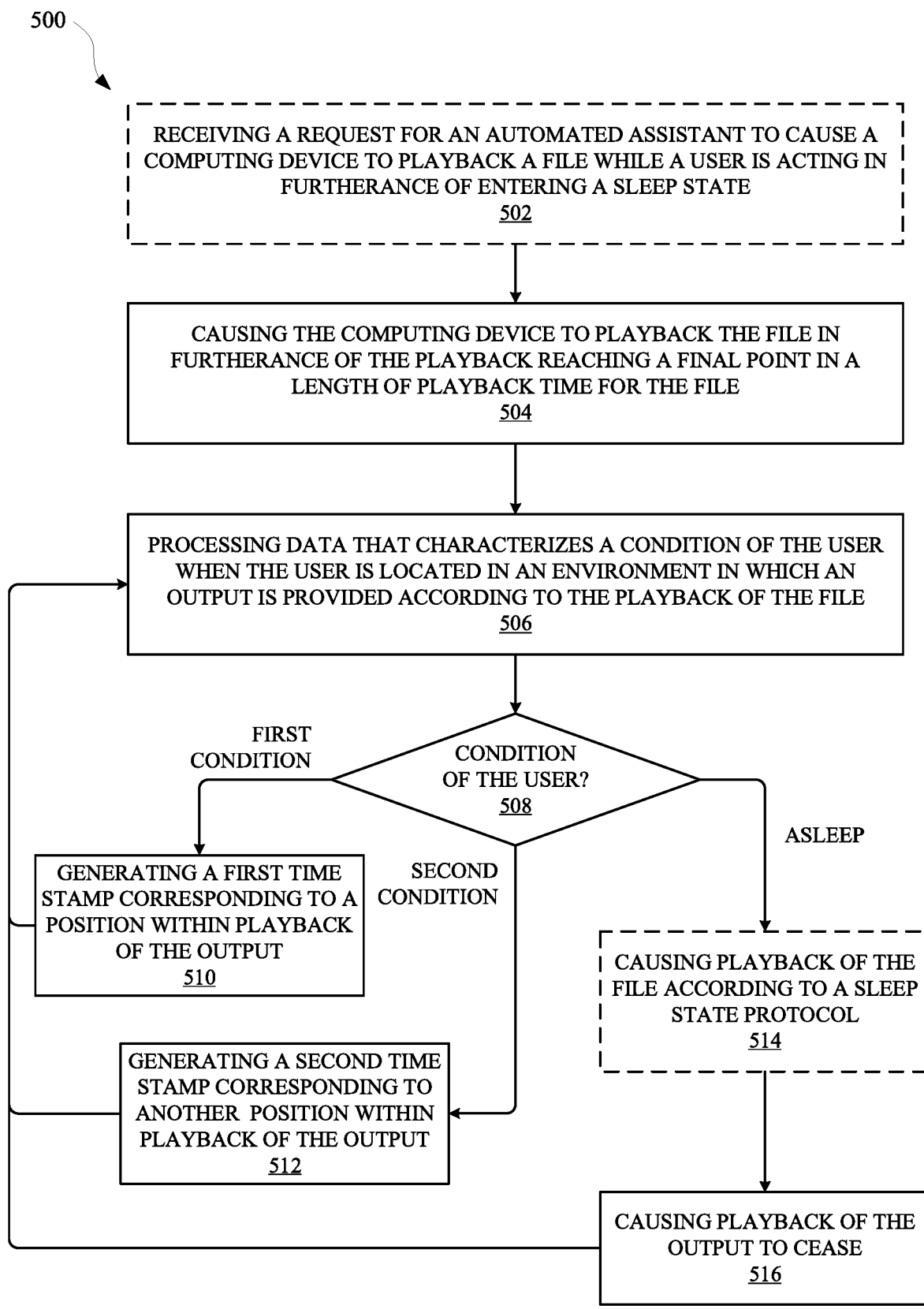
FIG. 5 illustrates a method for identifying timestamps corresponding to a temporal location within of an output that a user transitioned between conditions and/or fell asleep.

FIG. 5 illustrates a method 500 for identifying timestamps corresponding to a temporal location within of an output that a user transitioned between conditions and/or fell asleep. The method 500 can be performed by one or more computing devices, applications, and/or any other apparatus or module capable of interacting with a computing device that is accessing a file. The method 500 can include an optional operation 502 of receiving a request for an automated assistant to cause a computing device to playback an output while a user is acting in furtherance of falling asleep. The output can correspond to a file, stream, and/or any other source of data that a computing device can process in order to provide an output that can perceived by the user. The output can, for example, correspond to a podcast that is stored at a server device, which is in communication with a client device via which the user accesses the automated assistant. The client device can be a computing device that includes an automated assistant interface, such as a microphone, and the user can cause the podcast to be output by the client device by providing a spoken utterance such as, "Assistant, play my podcast."

The method 500 can further include an operation 504 of causing the computing device to provide the output in furtherance of the playback reaching a final point in a length of playback time for the data upon which the output is based. For instance, the podcast can have a length of playback, such as 1 hour, and the automated assistant can initially cause the podcast to begin at a first timestamp 0:00. The user can provide the spoken utterance for initializing playback of the podcast when the user has initially lied down on their couch, in furtherance of taking a nap. Furthermore, although the user has provided the spoken utterance to the client device, the output can be provided from the client device and/or a separate client device that is capable of providing an output that the user can comprehend when the user is on their couch. For instance, the user can provide the spoken utterance to their standalone speaker-display device, and the output can be initialized at their television, at least based on their television being connected to an audio system capable of more readily providing the output to the user.

The method 500 can further include an operation 506 of processing data that characterizes a condition of the user when the user is located in an environment in which an output is provided according to the playback of the file. The data can be provided by one or more different computing devices, such as one or more client devices located within the environment and/or connected to a network available in the environment, and/or one or more server devices, such as a server device that hosts at least a portion of the automated assistant and/or other data. For instance, the data can be provided by a wearable device that the user is wearing when the user initially causes playback of the podcast to occur. The data provided by the wearable device can include physiological data, which can be processed to at least assist in determining the condition of the user. Additionally, or alternatively, the data can be provided by a client device that is located within the environment with the user, and can therefore detect various environmental characteristics of the environment, and/or any particular characteristics exhibited by the user. For instance, the client device can include a microphone configured to be responsive to noises made by the user, devices, inanimate objects, and/or any other feature of the environment. The data from the client device can provide an indication of how active the user currently is, and therefore be used to determine a condition or state of the user.

The method 500 can further include an operation 508 of determining a condition of the user. The condition of the user can be based on the data collected from one or more different sources. Additionally, or alternatively, the data can characterize a frequency of motion of the user, a physiological condition of the user, and/or any other feature of a user that can indicate a state of the user. When the user is determined to be in a first condition, the method 500 can proceed to operation 510 of generating a first time stamp corresponding to a position within the playback of the output (e.g., the podcast). In order to determine that the user is in the first condition, the data can be processed to determine whether the user is stationary and/or has been stationary for a threshold period of time (e.g., when the user has initially lied down on their couch). The threshold period of time can be pre-determined or learned, by the client device, over time in order to more accurately determine when the user is in the first condition. Additionally, or alternatively, in order to determine that the user is in the first condition, the data can be processed to determine that a physiological attribute of the user indicates that the user is exhibiting an initial condition of relaxation relative to their previous condition. For instance, the data can be provided by a wearable device that provides at least some amount of data corresponding to one or more physiological attributes of the user, such as heartrate, respiratory rate, blood pressure, blood-oxygen level, frequency of motion, and/or any other physiological attribute. When one or more physiological attributes satisfy one or more respective conditions (e.g., heart rate and/or respiratory rate satisfy particular thresholds), the user can be considered to be in a first condition.

In response to determining that the user is in the first condition, a first time stamp can be generated. The first time stamp can correspond to a position within playback of the output being provided by the client device. For instance, if the podcast initially began at time stamp 0:00, and 15 minutes later the user was determined to be in the first condition, the first time stamp can be 15:00. In this way, although the user may not be asleep within the first condition, the user entering the first condition can nonetheless be an indication that the user may be paying more or less attention to the podcast or other output, relative to just before the user entered the first condition. The method 500 can return to operation 506 where additional data continues to be processed to determine whether the user is still in the first condition or has transitioned between conditions and/or other states.

When the user is determined to have transitioned to the second condition, the method 500 can proceed to operation 512 of generating a second time stamp corresponding to another position within playback of the output. The data can indicate that the user has transitioned to the second condition when one or more conditions are satisfied by the data. For instance, the data can characterize one or more physiological attributes, as discussed herein, and when one or more physiological attributes satisfy one or more conditions. In some implementations, when a particular physical attribute goes beyond a threshold associated with the first condition, the user can be considered to be in the second condition. For instance, when a heartrate of the user falls below a threshold corresponding to the first condition, the user can be considered to be in a second condition. Additionally, or alternatively, when a respiratory rate falls within a learned and/or dynamic threshold corresponding to the second condition, the user can be considered to be within the second condition. It should be noted that any number of conditions can be defined per user. For instance, depending on one or more different medical conditions of the user, a user may have multiple conditions that they transition between, therefore, operations of the automated assistant, the client device, and/or any other device can operate according to such conditions.

In response to determining that the user has transitioned to the second condition, a second time stamp can be generated. The second time stamp can correspond to another temporal position within the playback of the output during which the user was determined to be in the second condition. For instance, when the output is a podcast that initially started at the time stamp 0:00, and the user was determined to be within the second condition 25 minutes later, the second time stamp can be 25:00. In this way, should the user subsequently fall asleep, the user will be able to start the podcast from first time stamp or the second time stamp, when they wake up.

When the user is determined to have transitioned to a sleep state or otherwise determined to have fallen asleep, the method 500 can proceed to an optional operation 514 of causing playback of the output according to a sleep state protocol. In other words, the output can be modified according to a sleep state protocol, which can cause the output to cease over a period of time. For instance, the sleep state protocol can cause the output to gradually decrease as long as physiological attributes remain relatively constant as the user remains in the sleep state. In this way, an abrupt ending to the output can be bypassed in order to provide a smoother transition for the environment to eventually no longer have any artificial noise emitted by the client device. Alternatively, or additionally, playback of the output can be transitioned into, or combined with, a different output, such as ambient noise. In other words, as the output continues while the user is asleep, a different output can gradually increase in amplitude simultaneously with the initial output (e.g., the podcast) gradually decreasing in amplitude. In some implementations, a slope of the increase or decrease in amplitude of the output or they different output can be based on one or more physiological attributes of the user. For instance, historical data can indicate that the user is a light sleeper and/or easily awoken by changes to noise. Therefore, the slopes for the increase in the different output and the decrease in the original output can be low relative to slopes assigned for other persons' sleep protocols, in order to mitigate perceivable changes in sound amplitude.

When the user is determined to have transitioned from the second state to the sleep state, and/or has otherwise been determined to be in the sleep state, the method 500 can proceed to operation 516 of causing playback of the output to cease. In some implementations, the output can cease when the user is determined to be asleep, and in other limitations the output can be modified such that a file or a stream, from which the output is based, can be switched to a different file or a different stream. In some implementations, although the output has ceased, additional data can be continually analyzed or processed according to the operation 506. In this way, should the user awake and exhibit characteristics associated with the first condition or the second condition, another output can be initialized in response. For example, although the user was listening to a podcast just before the output of the podcast with ceased, should the user awaken after the podcast has ceased, a different output, such as ambient noise, can be the subject of playback that is based on a different file or a different stream. One more characteristics of the different output can be selected according to whether the user is within the first condition, the second condition, or is asleep, as discussed herein.

Figure 6:
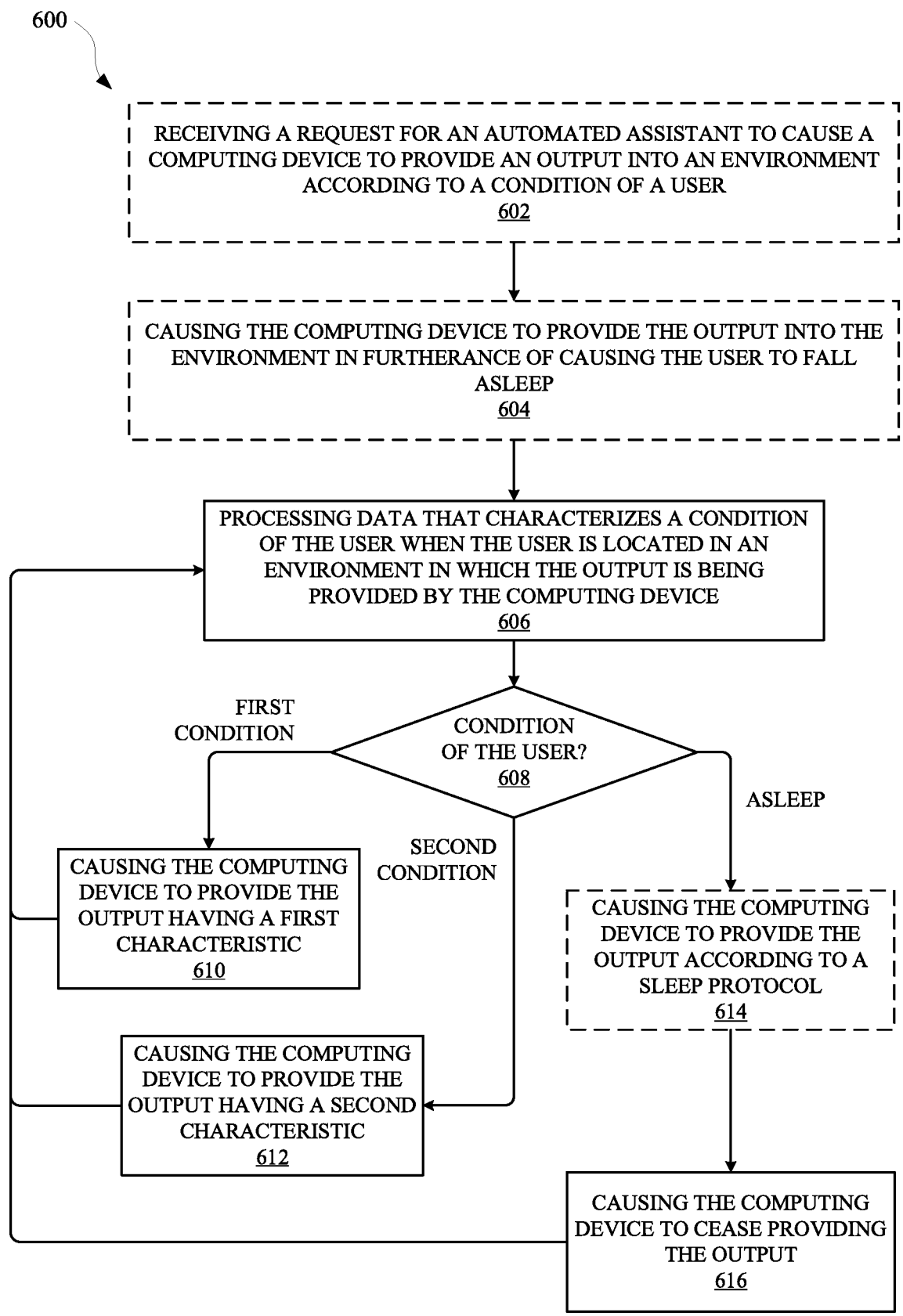
FIG. 6 illustrates a method for modifying an output of a computing device according to a condition of a user.

FIG. 6 illustrates a method 600 for modifying an output of a computing device according to a condition of a user. The method 600 can be performed by one or more computing devices, applications, and/or any other apparatus or module capable of modifying an output of a computing device. The method 600 can optionally include an operation 602 of receiving a request for an automated assistant to cause a computing device to provide an output into an environment according to a condition of a user. Specifically, the user can provide the spoken utterance to a client device that includes an automated assistant interface, and the spoken utterance can be, "Assistant, play ambient noise until I fall asleep." The spoken utterance can be received at the automated assistant interface, converted into audio data, and transmitted to a separate server device for processing. The server device can then respond with an action for the client device to perform, and accordingly initialize playback of the ambient noise.

In some implementations, depending on the condition of the user, the automated assistant can optionally indicate that automated assistant heard the spoken utterance from the user by causing playback of ambient noise, and/or any other output from a modality that is different from an output or modality that the automated assistant would otherwise use to acknowledge receipt of a spoken utterance. For example, when the user provides a spoken utterance after entering their bedroom past a particular time, the client device that receives the spoken utterance can cause playback of an ambient noise, such as rainforest sounds. In this way, should another person be in the room sleeping already, the other person would not be disturbed by the automated assistant responding with a loud, natural language output, such as "Ok," or any other acknowledgement of receipt of a spoken utterance. Rather, in response to a spoken utterance, an output that is less abrupt can be output from the client device in order to indicate to the user that the spoken utterance was received by the automated assistant.

In some implementations, the output provided in response to a spoken utterance from a particular user can change from user to user. For example, a first user can provide a spoken utterance when entering their bedroom at night, and a client device within their bedroom can output rainforest noises in order to indicate that the automated assistant has acknowledged receipt of the spoken utterance. Furthermore, a second user can provide the spoken utterance when entering the bedroom at night, and the client device within their bedroom can output classical music. Preferences for responsive sounds and/or other outputs can be learned over time as the user interacts with the automated assistant and/or any combination thereof. In some implementations, a first user may prefer that the automated assistant confirm acknowledgement by responding with ambient noise, while a second user may prefer that the automated assistant confirm that acknowledgement by emitting one or more patterns of light. Certain preferences for outputs can be based on the user that is speaking, a condition of the user, one or more conditions of one or more other users, and/or any other data from which a preference can be based upon.

The method 600 can further include an optional operation 604 of causing the computing device to provide the output into the environment in furtherance of causing the user to fall asleep. The client device to can begin emitting ambient noise while the user is acting in furtherance of falling asleep. The ambient noise can have one or more characteristics, which can be modified according to one more computing devices that are, for example, tasked with ensuring that the ambient noise is encouraging the user to fall asleep, instead of regressing away from falling asleep. Initially, the one or more characteristics of the output can be based on a default preference, a preference previously set by the user, and/or a detected condition at the time the output started, or just before the output started. For instance, if the user provided the spoken utterance as a whisper to the automated assistant, the automated assistant can capture the amplitude of the whisper as part of the condition in which the user provided the spoken utterance. The output can then be at least partially based on the condition, and, specifically, can be based on an amplitude of the spoken utterance provided to the automated assistant.

The method 600 can further include an operation 606 of processing data that characterizes a condition of the user when the user is located in an environment in which the output is being provided by the computing device. As discussed herein, data that characterizes a condition of the user can be provided from one or more different applications, devices, and/or any other apparatus or module capable of providing data. In some implementations, data used to determine a condition can include temporal data corresponding to a time of day, motion data corresponding to an amount of motion within one or more environments, audio data corresponding to the spoken utterance and/or any other noises associated with the user and/or the environment, schedule data based on a stored calendar or schedule(s) of one or more users, physiological data corresponding to one or more physiological attributes of one or more users, and/or any other information from which a condition of a user can be determined.

The method 600 can further include an operation 608 of determining a condition of the user. As discussed herein, the condition of the user can be based on data collected from one or more different sources. When the data indicates that the user is in a first condition, the method 600 can proceed to an operation 610 of causing the computing device to provide the output such that the output has a first characteristic.

When the user is in the first condition, the data can indicate that the user is in a more relaxed state than a previous state or another state they have otherwise been in for a majority of a day. For instance, a user can be considered to be in the first condition when their heartrate was an average of 70 beats per minute (bpm) for a majority of the day, and their wearable device currently indicates their heartrate is 65 bpm (e.g., less than 95% of the bpm for the majority of the day, or any other percentage threshold). In some implementations, the user can be considered to be in a first condition in response to the user providing a request to the automated assistant indicating that the user will be attempting to fall asleep or otherwise relax. For instance, in response to the automated assistant receiving the spoken utterance, "Assistant, play ambient noise until I fall asleep," the automated assistant can determine that the user is intending to fall asleep based on the content of the spoken utterance (e.g., " . . . until I fall asleep."). In some implementations, for purposes of identifying one or more characteristics to select for modifying the output (e.g., the ambient noise), the automated assistant can consider the user in the first condition until additional data indicates otherwise.

When the user is determined to be in the first condition and the output of the computing device is caused to have a first characteristic according to operation 610, the method 600 can return to operation 608, in which additional data can be processed. The additional data can be processed to determine whether the user is still in the first condition or has transitioned out of the first condition (e.g., to a different condition and/or has fallen asleep). When the user is determined to have transitioned from the first condition to the second condition, and/or otherwise has entered the second condition, the method 600 can proceed to operation 612 of causing the computing device to provide the output such that the output has a second characteristic.

In some implementations, the second characteristic can correspond to an amplitude of the output that is different from a previous amplitude corresponding to the first characteristic. For example, the output can be an audio output and the first characteristic can be an amplitude that is greater than an amplitude assigned for the second characteristic. In other words, when the user is determined to have transitioned from the first condition to the second condition, the audio output will decrease in amplitude. In some implementations, the first characteristic and the second characteristic can be associated with an equalization of an audio output. Therefore, in response to the user transitioning from the first condition to the second condition, amplitudes of one or more ranges of frequencies can be different according to how the first characteristic and the second characteristic are respectively defined. For example, the first characteristic can have a flat equalization, such that no change is made to the equalization of an initial source of the output, and the second characteristic can operate as a high pass, low pass, and/or band pass filter, thereby limiting an amplitude of particular branches of frequencies of the output. As a result, when the user transitions from the first condition to the second condition, higher frequency sounds, lower frequency sounds, and/or middle frequency sounds, and/or a combination thereof, will be adjusted in order to mitigate disruptions to the user eventually reaching a sleep state or otherwise falling asleep.

In some implementations, when the output is a visual and/or audio output, the first characteristic and the second characteristic can correspond to properties of light being admitted as part of the output. For instance, if the user has requested that the automated assistant play a movie until the user falls asleep, a brightness of the display panel that is outputting the movie can be adjusted in response to the user transitioning from the first condition to the second condition. Alternatively, or additionally, an equalization of the frequencies of light being emitted by the display panel can be adjusted in response to the user transitioning from the first condition to the second condition. For instance, when the user is determined to have transitioned from the first condition to the second condition, an amount of blue light apparent in the output from the display panel can be decreased in response. In some implementations, one or more properties of light can be adjusted in response to determining that the user has transitioned between different conditions, has fallen asleep, and/or has woken up.

When the user is determined to have transitioned from the second state to the sleep state, or has otherwise fallen asleep, the method 600 can proceed to an optional operation 614 of causing the computing device to provide the output according to a sleep protocol. The operation 614 can be the same as the operation 514 discussed with respect the method 500, and/or can be executed and/or modified according to any details discussed herein. For instance, in some implementations, when the output is a visual and/or audio-visual output, an amplitude or brightness of the light can be gradually decreased as the user remains asleep. The brightness can be decreased until eventually, at operation 616, the computing device can be caused to cease providing the output. In some implementations, one or more characteristics of light and one or more characteristics of audio can be adjusted concurrently while the user remains asleep in order to mitigate interruptions of the sleep of the user via abrupt changes in the environment. In some implementations, one or more characteristics of the light and/or the audio can be adjusted according to you changes in the data as the user remains asleep, and/or physiological attributes of the user as the user remains asleep. For instance, changes in one or more characteristics of the audio and/or video can be based on a respiratory rate of the user and, optionally, whether such a basis for the output has been previously determined to assist the user with staying asleep.

When the user is determined to have transitioned from the second state into the sleep state, and/or has otherwise entered the sleep state, the method 600 can proceed to operation 616 of causing the computing device to cease providing the output. The output can be stopped in order to eliminate further unnecessary consumption of processing and/or network bandwidth. Furthermore, despite the output being ceased at the computing device, the method 600 can proceed back to operation 606, wherein additional data can be processed in order to determine whether the user has transitioned out of the sleep state, or is expected to transition out of a sleep state. For instance, if the user happens to have a dream that wakes them up, the additional data can characterize the sudden motion, noise, and/or other environmental features affected by the user waking up. The data can be processed in order to identify a condition in which the user has transitioned into. For example, if the user has transitioned into the first condition, the method 600 can proceed from operation 608 to operation 610. The output can be reinitialized as a result, in order to encourage the user to again progress towards a sleep state, assuming that the user has woken up within a time period that they typically prefer to be asleep.

Figure 7:
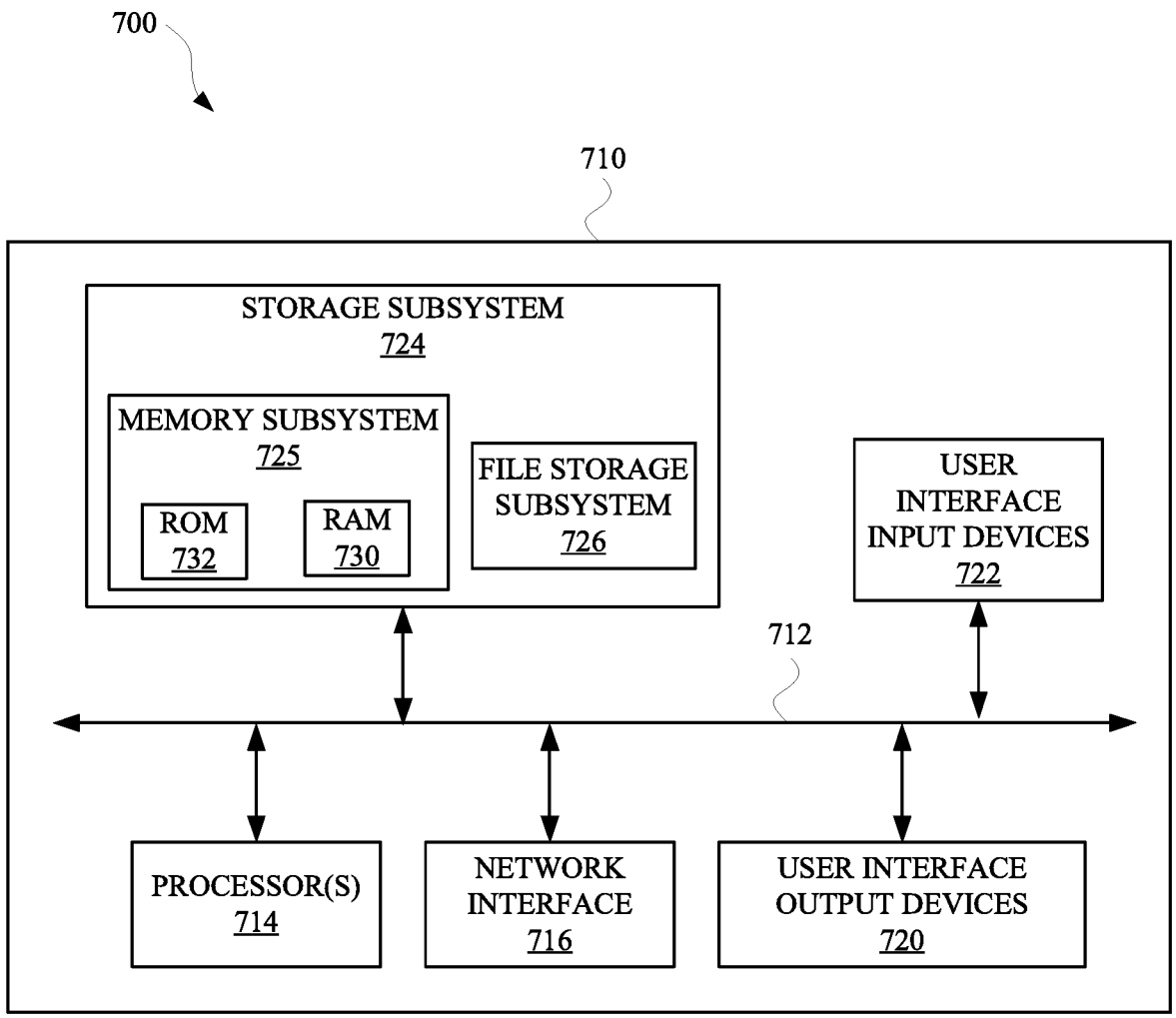
FIG. 7 is a block diagram of an example computer system.

FIG. 7 is a block diagram of an example computer system 710. Computer system 710 typically includes at least one processor 714 which communicates with a number of peripheral devices via bus subsystem 712. These peripheral devices may include a storage subsystem 724, including, for example, a memory 725 and a file storage subsystem 726, user interface output devices 720, user interface input devices 722, and a network interface subsystem 716. The input and output devices allow user interaction with computer system 710. Network interface subsystem 716 provides an interface to outside networks and is coupled to corresponding interface devices in other computer systems.

User interface input devices 722 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 710 or onto a communication network.

User interface output devices 720 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 710 to the user or to another machine or computer system.

Storage subsystem 724 stores programming and data constructs that provide the functionality of some or all of the modules described herein. For example, the storage subsystem 724 may include the logic to perform selected aspects of method 500, method 600, and/or to implement one or more of first computing device 106, first computing device 206, first computing device 306, second computing device 110, second computing device 210, second computing device 310, server device 402, computing device 418, other computing devices 434, and/or any other modules or apparatuses discussed herein.

These software modules are generally executed by processor 714 alone or in combination with other processors. Memory 725 used in the storage subsystem 724 can include a number of memories including a main random access memory (RAM) 730 for storage of instructions and data during program execution and a read only memory (ROM) 732 in which fixed instructions are stored. A file storage subsystem 726 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 726 in the storage subsystem 724, or in other machines accessible by the processor(s) 714.

Bus subsystem 712 provides a mechanism for letting the various components and subsystems of computer system 710 communicate with each other as intended. Although bus subsystem 712 is shown schematically as a single bus, alternative implementations of the bus subsystem may use multiple busses.

Computer system 710 can be of varying types including a workstation, server, computing cluster, blade server, server farm, or any other data processing system or computing device. Due to the ever-changing nature of computers and networks, the description of computer system 710 depicted in FIG. 7 is intended only as a specific example for purposes of illustrating some implementations. Many other configurations of computer system 710 are possible having more or fewer components than the computer system depicted in FIG. 7.

In some implementations, a method implemented by one or more processors is set forth as including operations such as causing a first output to be emitted by a computing device into an environment when a user is located within the environment, wherein the computing device is configured to adjust at least one characteristic of provided output according to one or more physiological attributes of the user. The method can further include accessing, when the first output is being emitted by the computing device, physiological data that characterizes the one or more physiological attributes of the user, wherein the physiological data is generated based on a sensor output of a separate device that is in communication with the computing device. The method can further include determining, based on the physiological data, that the user has progressed closer to a sleep state or has progressed to the sleep state; and causing, in response to determining that the user has progressed closer to the sleep state or is in the sleep state, a second output to be emitted by the computing device into the environment, wherein the second output is emitted with the at least one characteristic being adjusted in response to determining that the user has progressed closer to the sleep state or is in the sleep state, and wherein the adjustment of the characteristic is configured to reduce a probability that the user will regress from the sleep state.

In some implementations, the first output and the second output comprise corresponding portions of media that has a total length of playback time, and the method further comprises: generating, in response to determining that the user has progressed closer to the sleep state or has progressed to the sleep state, a timestamp, corresponding to a temporal position within the total length of playback time, at which the user progressed closer to the sleep state or progressed to the sleep state during playback of the media. In some implementations, the method can further include receiving, subsequent to generating the timestamp and halting output of the media, a request from the user to resume playback of media; and causing, in response to receiving the request from the user, playback of the media to resume from the temporal position corresponding to the timestamp. In some implementations, the method can further include in response to determining that the user has progressed closer to the sleep state or has progressed to the sleep state: causing playback of separate media, and causing playback of the media to cease subsequent to determining that that the user has progressed closer to the sleep state or has progressed to the sleep state. In some implementations, the first output is a first light output and the second output is a second light output, and the method further comprises: determining, prior to causing the first output to be emitted by the computing device into the environment, that the user has moved across a portion of the environment, wherein causing the first output to be emitted by the computing device into the environment is in response to determining that the user has moved across the portion of the environment. In some implementations, the first light output corresponds to a higher color temperature of light and/or a higher brightness of light, relative to the second light output. In some implementations, the separate device is a wearable device that is worn by the user and that includes one or more sensors that provided the sensor output.

In other implementations, a method implemented by one or more processors is set forth as including operations such as receiving, from a user, a spoken utterance corresponding to a request for an automated assistant to cause media to be rendered, the media having a fixed duration with a total length of playback time. The method can further include in response to receiving the spoken utterance, causing a computing device, from which the automated assistant is accessible, to render the media in furtherance of the media reaching a final point in the total length of the playback time. The method can further include processing data that characterizes one or more physiological attributes of the user when the user is located in an environment in which the media is being rendered. The method can further include determining, based on processing the data, that the user has progressed closer to a sleep state or to the sleep state; and generating, in response to determining that the user has progressed closer to the sleep state or to the sleep state, a timestamp corresponding to a temporal position, within the total length of playback time, at which the user progressed closer to the sleep state or to the sleep state during playback of the media.

In some implementations, the method can further include causing the computing device to continue performing playback of the media subsequent to generating the timestamp and determining that the user has progressed closer to the sleep state or to the sleep state. In some implementations, the method can further include subsequent to generating the timestamp and determining that the user has progressed closer to the sleep state or to the sleep state: processing additional data that characterizes the one or more physiological attributes of the user, and determining, based on processing the additional data, that the user has progressed to the sleep state or to a deeper state of sleep. In some implementations, the method can further include generating, in response to determining that the user has progressed to the sleep state or to the deeper state of sleep, a separate timestamp corresponding to a separate temporal position, within the total length of playback time, at which the user was determined to have progressed to the sleep state or to the deeper state of sleep. In some implementations, the method can further include causing playback of the media to cease subsequent to determining that the user has progressed to the sleep state or to the deeper state of sleep. In some implementations, the method can further include causing, subsequent to playback of the media ceasing and/or concurrent with the playback of the media ceasing, playback of separate media to be initialized in response to determining that the user has progressed to the sleep state or to the deeper state of sleep. In some implementations, one or more characteristics of the playback of the separate media are at least temporarily based on, or shared with, one or more other characteristics of the playback of the media. In some implementations, the one or more other characteristics includes a volume of audio corresponding to the playback of the media or a level of brightness corresponding to a playback of the media.

In yet other implementations, a method implemented by one or more processors is set forth as including operations such as processing data that is based on one or more sensors in an environment to determine a current condition of a dynamic condition of a user, wherein sound is being emitted, in the environment, from a computing device that is configured to adjust an adjustable characteristic of the sound based on the dynamic condition of the user. The method can further include determining, based on processing the data, whether a present value, of the adjustable characteristic of the sound, is unsuitable for the current condition of the user, wherein determining whether the present value is unsuitable for the current condition of the user comprises determining whether the present value will increase a probability that the user will regress away from a desired condition. The method can when the present value is determined to be unsuitable for the current condition of the user: selecting an alternate value for the adjustable characteristic of the sound, wherein the alternate value is selected to decrease the probability of the user regressing from the desired condition, and causing the computing device to transition the sound from exhibiting the present value to the alternate value.

In some implementations, the present value of the sound corresponds to a volume of the sound being emitted into the environment and the alternate value of the sound corresponds to a lower volume of sound, the lower volume of sound being lower relative to the volume of the present value of the sound. In some implementations, the method can further include determining whether the present value of the sound will increase the probability that the user will regress away from the desired condition further based on a correspondence between the current condition of the user and the present value of the sound. In some implementations, the one or more sensors in the environment, on which the data is based, comprise a sensor that is integral to a wearable computing device being worn by the user. In some implementations, the data includes circumstantial data that is based on outputs from multiple different computing devices connected to a local area network with the computing device. In some implementations, the data further characterizes a predicted event that is associated with an interruption of the user reaching the desired condition, and the method further comprises: determining, based on processing the data, that the predicted event is expected to occur and cause the interruption, wherein determining whether the present value of the sound is unsuitable for the desired condition of the user is further based on determining that the predicted event is expected to occur. In some implementations, the method can further include determining whether the present value of the sound will increase the probability that the user will regress away from the desired condition further based at least on determining that the predicted event is expected to occur, wherein the probability is based at least on a historical responsiveness of the user to a previous sound exhibiting the present value.

In some implementations, the method can further include subsequent to causing the computing device to transition the sound from exhibiting the present value to the other characteristic: determining that the user has provided a spoken utterance corresponding to a request for the automated assistant to cause a particular output to be provided according to the request, and causing the particular output to be provided based on the current condition of the user. In some implementations, wherein causing the particular output to be provided based on the current condition of the user includes: selecting, based on the current condition of the user, one or more particular for the particular output, wherein the one or more particular values are selected to decrease the probability of the user regressing from the current condition. In some implementations, the particular output requested by the user is an audio output and the one or more particular values correspond to characteristics that include a volume of the audio output, and/or the particular output is a visual output and the one or more particular values correspond to characteristics that include a brightness and/or color temperature of the visual output.

In yet other implementations, a method implemented by one or more processors of an assistant computing device is set forth as including operations such as transitioning the assistant computing device from a first state to a second state, wherein in the first state the assistant computing device does not perform certain processing of audio data detected via one or more microphones of the assistant computing device, and wherein in the second state the assistant computing device performs the certain processing of audio data detected via the one or more microphones. In some implementations, the method can further include, responsive to transitioning the assistant computing device to the second state, and for a duration of the second state: rendering ambient audio via one or more speakers of the assistant computing device; and responsive to cessation of the second state: ceasing the rendering of the ambient audio.

In some implementations, the method can further include, when in the first state, monitoring for occurrence of an invocation phrase by processing audio data detected via the one or more microphones using only a local invocation model stored locally at the assistant computing device; wherein transitioning the assistant computing device from the first state to the second state is based on detecting an occurrence of the invocation phrase in a portion of the audio data. In some implementations, the method can further include selecting the ambient audio based on the ambient audio being stored in association with a user profile that is determined based at least in part on further analysis of the portion of the audio data. In some implementations, the method can further include determining a volume for the rendering of the ambient audio, wherein rendering the ambient audio is at the determined volume. In some implementations, determining the volume is based on one or more of: a level of background noise as detected via the one or more microphones, an estimated distance of an active user of the assistant computing device, or one or more physiological characteristics of the active user. In some implementations, the certain processing comprises one or more of: transmitting the audio data to a remote automated assistant server, or speech-to-text processing. In some implementations, in the first state the assistant device is rendering a response that is responsive to a previous request received via the assistant device, and wherein transitioning the assistant computing device from the first state to the second state occurs automatically in response to completion of rendering the response.

In situations in which the systems described herein collect personal information about users (or as often referred to herein, "participants"), or may make use of personal information, the users may be provided with an opportunity to control whether programs or features collect user information (e.g., information about a user's social network, social actions or activities, profession, a user's preferences, or a user's current geographic location), or to control whether and/or how to receive content from the content server that may be more relevant to the user. Also, certain data may be treated in one or more ways before it is stored or used, so that personal identifiable information is removed. For example, a user's identity may be treated so that no personal identifiable information can be determined for the user, or a user's geographic location may be generalized where geographic location information is obtained (such as to a city, ZIP code, or state level), so that a particular geographic location of a user cannot be determined. Thus, the user may have control over how information is collected about the user and/or used.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

I claim:

1. A method, implemented by one or more processors of an assistant computing device, comprising:
in response to detecting an occurrence of an invocation at the assistant computing device:
transitioning the assistant computing device from a first state to a second state, wherein in the first state the assistant computing device does not perform certain processing of audio data detected via one or more microphones of the assistant computing device, and wherein in the second state the assistant computing device performs the certain processing of audio data detected via the one or more microphones;
responsive to transitioning the assistant computing device to the second state, and for a duration of the second state:
rendering ambient audio via one or more speakers of the assistant computing device, wherein the rendering is for the duration of the second state in which the assistant computing device performs the certain processing of audio data, and wherein the duration of the second state begins with transitioning the assistant computing device from the first state to the second state, in which the automated assistant performs the certain processing of audio data, and wherein the duration of the second state ends with the cessation of the second state; and
responsive to cessation of the second state:
ceasing the rendering of the ambient audio.

2. The method of claim 1, further comprising:
when in the first state:
monitoring for occurrence of an invocation phrase by processing audio data detected via the one or more microphones using only a local invocation model stored locally at the assistant computing device,
wherein transitioning the assistant computing device from the first state to the second state is based on detecting the occurrence of the invocation phrase in a portion of the audio data.

3. The method of claim 1, further comprising:
when in the first state:
monitoring for occurrence of an invocation gesture by processing video data detected via one or more cameras of the assistant computing device,
wherein transitioning the assistant computing device from the first state to the second state is based on detecting the occurrence of the invocation gesture in a portion of the video data.

4. The method of claim 1, further comprising:
selecting the ambient audio based on the ambient audio being stored in association with a user profile that is determined based at least in part on further analysis of the portion of the audio data.

5. The method of claim 1, further comprising:
determining a volume for the rendering of the ambient audio, wherein rendering the ambient audio is at the determined volume.

6. The method of claim 5, wherein determining the volume is based on one or more of:
a level of background noise as detected via the one or more microphones, an estimated distance of an active user of the assistant computing device, or one or more physiological characteristics of the active user.

7. The method of claim 1, wherein the certain processing comprises one or more of:
transmitting the audio data to a remote automated assistant server and/or speech-to-text processing.

8. The method of claim 1, wherein, in the first state:
rendering a response that is responsive to a previous request received via the assistant device, and wherein transitioning the assistant computing device from the first state to the second state occurs automatically in response to completion of rendering the response.

9. A method, implemented by one or more processors of an assistant computing device, comprising:
monitoring for occurrence of an invocation phrase by processing audio data detected via the one or more microphones;
in response to detecting the invocation phrase in a portion of the audio data:
rendering ambient audio via one or more speakers of the assistant computing device;
performing, while rendering the ambient audio, certain processing, of audio data detected via the one or more microphones, that is not performed prior to detecting the invocation phrase, wherein the certain processing includes processing a request that is included in the audio data, and wherein performing the certain processing of the audio data begins when rendering the ambient audio begins and ends when rendering the ambient audio ends; and
rendering a response that is responsive to the request; and
in response to starting rendering of the response:
ceasing the rendering of the ambient audio.

10. The method of claim 9, wherein monitoring for occurrence of the invocation phrase by processing audio data detected via the one or more microphones includes using only a local invocation model stored locally at the assistant computing device.

11. The method of claim 9, wherein the certain processing comprises speech-to-text processing.

12. The method of claim 9, further comprising:
processing the audio data to determine a user profile for a user that uttered the invocation phrase; and
selecting the ambient audio based on the ambient audio being stored in association with the user profile.

13. The method of claim 9, further comprising:
determining a volume for the rendering of the ambient audio, wherein rendering the ambient audio is at the determined volume.

14. The method of claim 13, wherein determining the volume is based on one or more of:
a level of background noise as detected via the one or more microphones, an estimated distance of an active user of the assistant computing device, or one or more physiological characteristics of the active user.

15. An assistant computing device, comprising one or more processors, and memory configured to store instructions that, when executed by one or more of the processors, cause one or more of the processors to perform operations that include:
in response to detecting an occurrence of an invocation at the assistant computing device:
transitioning the assistant computing device from a first state to a second state, wherein in the first state the assistant computing device does not perform certain processing of audio data detected via one or more microphones of the assistant computing device, and wherein in the second state the assistant computing device performs the certain processing of audio data detected via the one or more microphones;
responsive to transitioning the assistant computing device to the second state, and for a duration of the second state:
rendering ambient audio via one or more speakers of the assistant computing device, wherein the rendering is for the duration of the second state in which the assistant computing device performs the certain processing of audio data, and wherein the duration of the second state begins with transitioning the assistant computing device from the first state to the second state, in which the automated assistant performs the certain processing of audio data, and wherein the duration of the second state ends with the cessation of the second state; and
responsive to cessation of the second state:
ceasing the rendering of the ambient audio.

16. The computing device of claim 15, wherein the operations further include:
when in the first state:
monitoring for occurrence of an invocation phrase by processing audio data detected via the one or more microphones using only a local invocation model stored locally at the assistant computing device,
wherein transitioning the assistant computing device from the first state to the second state is based on detecting the occurrence of the invocation phrase in a portion of the audio data.

17. The computing device of claim 15, wherein the operations further include:
selecting the ambient audio based on the ambient audio being stored in association with a user profile that is determined based at least in part on further analysis of the portion of the audio data.

18. The computing device of claim 15, wherein the operations further include:
determining a volume for the rendering of the ambient audio, wherein rendering the ambient audio is at the determined volume.

19. The computing device of claim 18, wherein determining the volume is based on one or more of:
a level of background noise as detected via the one or more microphones, an estimated distance of an active user of the assistant computing device, or one or more physiological characteristics of the active user.

20. The computing device of claim 15, wherein the certain processing comprises one or more of:
    transmitting the audio data to a remote automated assistant server, or speech-to-text processing.

\* \* \* \* \*